US011040043B2

(12) United States Patent
Masini-Eteve et al.

(10) Patent No.: US 11,040,043 B2
(45) Date of Patent: Jun. 22, 2021

(54) TRANSDERMAL PHARMACEUTICAL COMPOSITIONS COMPRISING ACTIVE AGENTS

(71) Applicant: Besins Healthcare Luxembourg SARL, Luxembourg (LU)

(72) Inventors: Valerie Masini-Eteve, Bourg-la-Reine (FR); Denis Canet, Paris (FR)

(73) Assignee: BESINS HEALTHCARE LUXEMBOURG SARL, Luxembourg (LU)

( * ) Notice: Subject to any disclaimer, the term of this patent is extended or adjusted under 35 U.S.C. 154(b) by 0 days.

(21) Appl. No.: 16/111,098

(22) Filed: Aug. 23, 2018

(65) Prior Publication Data
US 2019/0160077 A1 May 30, 2019

Related U.S. Application Data

(63) Continuation of application No. 12/912,310, filed on Oct. 26, 2010, now Pat. No. 10,080,760.

(60) Provisional application No. 61/255,241, filed on Oct. 27, 2009.

(30) Foreign Application Priority Data

Dec. 10, 2009 (EP) .................................... 09178762

(51) Int. Cl.
| *A61K 31/56* | (2006.01) |
| *A61K 9/00* | (2006.01) |
| *A61K 9/06* | (2006.01) |
| *A61K 31/565* | (2006.01) |
| *A61K 31/566* | (2006.01) |
| *A61K 31/568* | (2006.01) |
| *A61K 31/57* | (2006.01) |
| *A61K 31/573* | (2006.01) |
| *A61K 47/10* | (2017.01) |
| *A61K 47/12* | (2006.01) |
| *A61K 47/14* | (2017.01) |

(52) U.S. Cl.
CPC ............ *A61K 31/56* (2013.01); *A61K 9/0014* (2013.01); *A61K 9/06* (2013.01); *A61K 31/565* (2013.01); *A61K 31/566* (2013.01); *A61K 31/568* (2013.01); *A61K 31/57* (2013.01); *A61K 31/573* (2013.01); *A61K 47/10* (2013.01); *A61K 47/12* (2013.01); *A61K 47/14* (2013.01)

(58) Field of Classification Search
CPC ........ A61K 31/56; A61K 9/0014; A61K 9/06; A61K 31/568; A61K 47/10
See application file for complete search history.

(56) References Cited

U.S. PATENT DOCUMENTS

| 4,906,169 | A | 3/1990 | Chien et al. |
| 5,232,703 | A | 8/1993 | Blank |
| 5,332,577 | A | 7/1994 | Gertner et al. |
| 5,778,984 | A | 8/1998 | Guenther et al. |
| 5,891,462 | A | 4/1999 | Carrara |
| 6,503,894 | B1 | 1/2003 | Dudley et al. |
| 6,582,724 | B2 * | 6/2003 | Hsu ..................... A61K 9/0014 424/443 |
| 7,611,727 | B2 | 11/2009 | Taravella et al. |
| 7,704,516 | B2 | 4/2010 | Drouin et al. |
| 10,080,760 | B2 | 9/2018 | Masini-Eteve et al. |
| 2003/0175329 | A1 | 9/2003 | Azarnoff et al. |
| 2004/0001861 | A1 | 1/2004 | Selzer et al. |
| 2004/0072810 | A1 | 4/2004 | Masini-Eteve et al. |
| 2004/0110732 | A1 | 6/2004 | Masini-Eteve et al. |
| 2004/0175416 | A1 | 9/2004 | Taravella et al. |
| 2005/0118242 | A1 | 6/2005 | Dudley et al. |
| 2006/0105041 | A1 | 5/2006 | Masini-Eteve |
| 2006/0239929 | A1 | 10/2006 | Dow et al. |
| 2007/0082039 | A1 | 4/2007 | Jones, Jr. et al. |
| 2007/0196325 | A1 | 8/2007 | Zhang et al. |
| 2008/0038220 | A1 | 2/2008 | Salin-Drouin |
| 2010/0048526 | A1 | 2/2010 | Taravella et al. |
| 2011/0118226 | A1 | 5/2011 | Masini-Eteve |
| 2012/0010245 | A1 | 1/2012 | Masini-Eteve |
| 2012/0122829 | A1 | 5/2012 | Taravella et al. |

FOREIGN PATENT DOCUMENTS

| EP | 0 364 211 A1 | 4/1990 |
| EP | 0 409 383 A2 | 1/1991 |
| EP | 0 672 422 | 3/1994 |
| EP | 0 737 477 A1 | 10/1996 |
| EP | 1 043 020 A1 | 10/2000 |
| EP | 0 811 381 B1 | 5/2003 |
| FR | 2518879 A | 7/1983 |
| FR | 2814074 A1 | 3/2002 |
| GB | 880276 | 10/1961 |
| JP | 2002-212105 | 7/2002 |
| RU | 2122396 C1 | 11/1998 |
| WO | WO 92/07590 A1 | 5/1992 |
| WO | WO 94/04157 A1 | 3/1994 |
| WO | WO 95/17896 A1 | 7/1995 |
| WO | WO 97/39743 A1 | 10/1997 |
| WO | WO 98/18417 A1 | 5/1998 |
| WO | WO 98/32465 A1 | 7/1998 |
| WO | WO 99/24041 | 5/1999 |

(Continued)

OTHER PUBLICATIONS

Vickers, "Stratum Corneum Reservoir for Drugs," Advances in Biology of Skin, vol. 12, pp. 177-189, Jan. 1, 1972.

(Continued)

*Primary Examiner* — Anna Pagonakis
(74) *Attorney, Agent, or Firm* — Foley & Lardner LLP

(57) ABSTRACT

The present invention provides compositions and methods for providing sustained release of an active agent through the skin of a subject, wherein a pharmaceutical percutaneous composition comprises at least one fatty acid ester and a therapeutically effective amount of active agent.

13 Claims, 10 Drawing Sheets

(56) References Cited

FOREIGN PATENT DOCUMENTS

| WO | WO 02/11768 A1 | 2/2002 |
|----|----|----|
| WO | WO 02/22132 A2 | 3/2002 |
| WO | WO 2006/110777 A1 | 10/2006 |

OTHER PUBLICATIONS

International Search Report dated Jan. 19, 2012 in application No. PCT/EP2010/066283.
Van Scott et al., "Typerkeratinization, Corneocyte Cohesion, and Alpha Hydroxy Acids," J. Am Acad Dermatol 11:867-879 (1984).
Office Action dated Jun. 11, 2007 in U.S. Appl. No. 10/393,077 (US 2004/0110732).
Office Action dated Oct. 20, 2006 in U.S. Appl. No. 10/393,077 (US 2004/0110732).
Office Action dated Jan. 26, 2006 in U.S. Appl. No. 10/393,077 (US 2004/0110732).
Database WPI, Derwent Publications Ltd., XP002260254 & JP 01 138288 A (Nonogawa Shoji), May 31, 1989.
Database WPI, Derwent Publications Ltd., XP 002260255 & KR 2002 013 248 A (Guju) & KR 2002 013 248, Feb. 20, 2002.
Office Action dated Jul. 12, 2012 by the Examiner in U.S. Appl. No. 13/353,667 (US 2012-0122829).
"Transdermal Therapeutic Systems," Good Clinical Practice, Jan. 2001, obtained online http://medi.ru/doc/991011.htm, accessed on Nov. 12, 2015.
Russian Office Action dated Nov. 16, 2015 in application No. 2012121708.
Walters, "Dermatological Formulation and Transdermal Systems," and "Formulation Exipients," Dermatological and Transdermal Formulations, Chapter III, pp. 319-325 and 437, 2002.

* cited by examiner

TRANSDERMAL PHARMACEUTICAL COMPOSITIONS COMPRISING ACTIVE AGENTS

PRIORITY

This application is a continuation of U.S. application Ser. No. 12/912,310, filed Oct. 26, 2010, which claims the benefit under 35 U.S.C. § 119(e) of U.S. Provisional Application No. 61/255,241 filed on Oct. 27, 2009, the entire contents of which are incorporated herein by reference in their entirety, and also claims the benefit under 35 U.S.C. § 119(a) of European Application No. EP 09178762.2, filed on Dec. 10, 2009.

FIELD OF THE INVENTION

Disclosed herein are compositions and methods for delivering a therapeutically active agent through the skin of a subject, e.g., to transdermal pharmaceutical compositions.

BACKGROUND

It is well known that certain therapeutically active agents are not suitable for oral administration for various reasons associated, inter alia, with either a high level of metabolism in the liver ("first pass effect") or a high level of gastrointestinal degradation. Transdermal or transmucosal formulations have been developed in order to circumvent these drawbacks. Specifically, pharmaceutical compositions for transdermal or transmucosal administration have several advantages over oral forms, including elimination of the problems associated with metabolism of the therapeutically active agent by the liver and with gastric degradation of the active agent. However, transdermal and transmucosal compositions face problems associated with the kinetics of passage of the therapeutically active agents from the surface of the skin into the bloodstream.

Indeed, the skin is a heterogeneous tissue which comprises two layers: the dermis and the outer most epidermis layer, which can be further divided into the stratum corneum and the viable epidermis. These layers provide the skin with barrier capacities against the entry of foreign substances such as drugs. The stratum corneum acts as a physical diffusive barrier, whereas the epidermis and dermis can provide in addition a biochemical or enzymatic barrier.

Studies concerning the absorption of therapeutically active agents by the skin have focused for the most part on improving the rate of absorption of the active agents ingredients through the skin, rather than paying any attention to the fate of the absorbed active agents. For example, the use of permeation enhancers was proposed in order to increase the initial rate of penetrated active agents through the skin. The term "permeation enhancer" generally refers to any molecule that promotes the reversible diffusion of an active agent through the skin or mucous membranes, and any solubilizing agent that promotes the partitioning of the active agent between the vehicle and the horny layer of the epidermis or of the mucous membranes. Most enhancers affect the stratum corneum barrier capacities, i.e., they reversibly alter the stratum corneum structure, thus increasing drug diffusivity and solubility. This indeed enhances skin penetration of the active agents, but this may also result in the direct absorption of a large amount of the drug through the tissues, leading to a peak active agent concentration in the blood in the immediate hours following the application of the composition. This initial peak is often followed by a trough in blood concentrations prior to the next application of the composition, which usually occurs many hours later, or once-a-day. Such a sudden rise of drug concentration in the blood could be dangerous for the patient as it may exceed the drug dose tolerated by the organism. In addition, as the whole dose of active agent is delivered to the bloodstream and tissues in the first hours following the application, the drug's intended effects may not endure until the next application.

There remains a need, therefore, for transdermal pharmaceutical compositions capable of delivering at least a part of their active content in a controlled-release manner, for example through temporary storage in the dermis.

SUMMARY

Described herein are sustained release transdermal pharmaceutical compositions, and methods of making and using them.

In accordance with some embodiments, there are provided sustained release pharmaceutical compositions for topical administration to a skin surface comprising: a pharmaceutically active agent comprising one or more steroids, a fatty acid ester, water, a C2-C6 monoalcohol and a fatty acid, wherein the weight:weight ratio of the fatty acid ester in the composition to the total active agent in the composition is at least 4:1 fatty acid ester:active agent. In some embodiments, the weight:weight ratio of fatty acid ester: active agent in the composition ranges from about 4:1 to about 20:1.

In some embodiments, the composition further comprises a co-solvent, such as propylene glycol. In some embodiments, the co-solvent is present in an amount ranging from 0.01% to 7%, by weight of the total weight of the pharmaceutical composition, or in an amount ranging from 3% to 7% by weight of the total weight of the pharmaceutical composition.

In some embodiments, the fatty acid ester is selected from the group consisting of ethyl oleate, isopropyl oleate, isopropyl myristate, isopropyl isostearate, isopropyl palmitate, ethyl octanoate, ethyl dodecanoate, ethyl linoleate, ethyl palmitoleate, ethyl isostearate and ethyl linolenate. In some embodiments, the fatty acid ester is the ester that would result from the reaction of the fatty acid formulated in the composition with an alcohol. In other embodiments, the fatty acid ester is not the ester that would result from the reaction of the fatty acid formulated in the composition with the alcohol formulated in the composition. In some embodiments, the fatty acid ester is present in an amount ranging from 0.01% to 5% by weight of the total weight of the pharmaceutical composition, or in an amount ranging from 0.05% to 2.4% by weight of the total weight of the pharmaceutical composition, or in an amount ranging from 0.1% to 2.2% by weight of the total weight of the pharmaceutical composition.

In some embodiments, the fatty acid is a C8-C22 fatty acid. In some embodiments, the fatty acid is selected from the group consisting of capric acid, lauric acid, myristic acid, palmitic acid, stearic acid, oleic acid, isostearic acid, palmitoleic acid, linoleic acid and linolenic acid. For example, in some embodiments, the fatty acid is oleic acid. In some embodiments, the fatty acid is present in an amount ranging from 0.01% to 5% by weight of the total weight of the pharmaceutical composition, or in an amount ranging from 0.05% to 3.5% by weight of the total weight of the pharmaceutical composition, or in an amount ranging from 1.0% to 3.0% by weight of the total weight of the pharmaceutical composition.

In specific embodiments, compositions comprise 2% ethyl oleate as the fatty acid ester, 2% oleic acid as the fatty acid, and 5% propylene glycol as the co-solvent, all by weight of the total weight of the pharmaceutical composition. In other specific embodiments, compositions comprise 0.3% ethyl oleate as the fatty acid ester, 0.3% oleic acid as the fatty acid, and 0.75% propylene glycol as the co-solvent, all by weight of the total weight of the pharmaceutical composition.

In some embodiments, the pharmaceutically active agent is selected from the group consisting of estrogens, anti-estrogens (or SERMs), androgens, anti-androgens, progestins, and mixtures thereof. In some embodiments, the pharmaceutically active agent is selected from estradiol and progesterone, and the fatty acid ester is ethyl oleate. In other specific embodiments, the pharmaceutically active agent is selected from testosterone and dihydrotestosterone (DHT), and the fatty acid ester is selected from ethyl oleate and isopropyl myristate. In some embodiments, the active agent is present in an amount ranging from 0.01% to 5% by weight of the total weight of the pharmaceutical composition.

In some embodiments, the alcohol is selected from the group consisting of ethanol, n-propanol, isopropanol, n-butanol, isobutanol, tert-butanol, and mixtures thereof. For example, in some embodiments, the alcohol is ethanol. In some embodiments, the alcohol is present in an amount ranging from 10% to 90% by weight of the total weight of the pharmaceutical composition, or in an amount ranging from 20% to 80% by weight of the total weight of the pharmaceutical composition, or in an amount ranging from 45% to 75% by weight of the total weight of the pharmaceutical composition.

In accordance with other embodiments there are provided methods of making a sustained release pharmaceutical composition for topical administration to a skin surface comprising mixing a pharmaceutically active agent comprising one or more steroids, a fatty acid ester, water, a C2-C6 monoalcohol and a fatty acid, wherein the weight:weight ratio of the fatty acid ester in the composition to the total active agent in said composition is at least 4:1 fatty acid ester:active agent. In some embodiments, the weight:weight ratio of fatty acid ester:active agent in the composition ranges from about 4:1 to about 20:1. Any composition as described above and below may be made by such methods.

In accordance with other embodiments there are provided methods for providing a sustained release of a pharmaceutically active agent through the skin of a subject, comprising topically administering to the skin of the subject a pharmaceutical composition comprising a pharmaceutically active agent comprising one or more steroids, a fatty acid ester, water, a C2-C6 monoalcohol and a fatty acid, wherein the weight:weight ratio of the fatty acid ester in the composition to the total active agent in the composition is at least 4:1 fatty acid ester:active agent. Any composition as described above and below may be used in such methods. In specific embodiments, the fatty acid ester is present in the composition in an amount ranging from 0.1% to 20% by weight of the total weight of the pharmaceutical composition.

In some embodiments, sustained release of the pharmaceutically active agent through the skin is observed at least 24 hours after its administration. In other embodiments, sustained release of the pharmaceutically active agent through the skin is observed at least 36 hours after its administration. In yet other embodiments sustained release of the pharmaceutically active agent through the skin is observed at least 48 hours after its administration.

DETAILED DESCRIPTION

Figure 1:
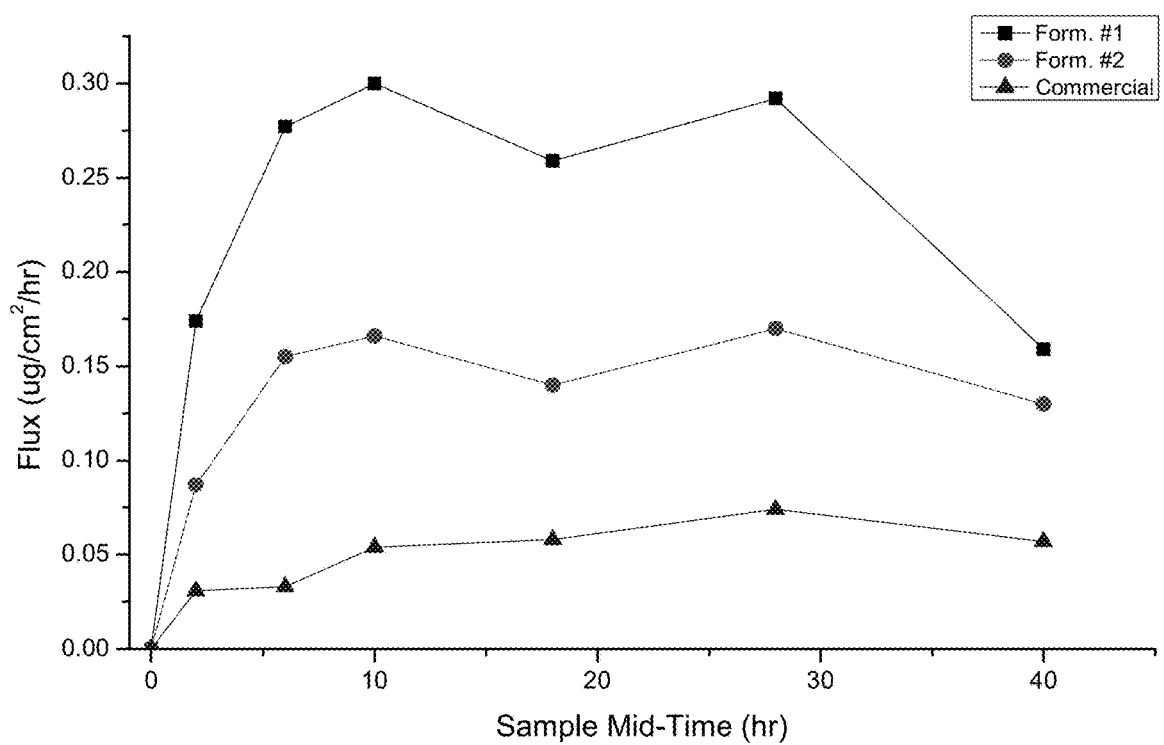
FIG. 1 represents the amount of progesterone delivered through the skin in 48 hours (flux, µg/cm2/hr) for the different formulations tested in Example 5. (■-Formulation 1; ●-Formulation 2; ▲-PROGESTOGEL® (1% progesterone hydroalcholic gel) (Besins Healthcare)).

Few studies have investigated whether transdermally administered active agents pass directly through the skin into the bloodstream, or whether they are first retained within a compartment within the skin that serves as an active agent storage depot, prior to being released into the circulation. It is known from the article entitled "Will cutaneous levels of absorbed material be systemically absorbed?" (*Drugs and Pharmaceutical Science*, Vol. 97, 235-239, 1999), that skin can behave as a storage depot for absorbed materials. For example, a skin storage depot for chemicals has been described by Vickers, *Adv Biol Skin*. Vol. 12, 177-89 (1972), to exist in the stratum corneum for topically applied lipophilic chemicals such as steroids.

However, as described herein, it has been found that a storage depot in the dermis can be more effective than a storage depot in the stratum corneum, and can provide a better means to regulate the diffusion kinetics of active agents in the tissues and a better effective drug delivery over time. Indeed, the dermis constitutes the majority of the skin mass. It contains a dense blood and lymphatic vasculature, and it is the site of drug absorption into the systemic circulation. The dermis, nevertheless, has rarely been targeted as a site for administration or deposition of substances, probably due to difficulty in controlling the layer of the skin in which the active agent is actually retained.

Thus, described herein are transdermal pharmaceutical compositions that exhibit advantageous properties and achieve advantageous results with regard to their drug delivery profiles. For example, embodiments of the compositions described herein achieve systemic delivery of therapeutically active agent(s) through the outer layers of the skin into the dermis, where a depot is formed from which the active agent is delivered into the bloodstream over an extended period of time, such as over a period of time of at least 12 hours, at least 24 hours, at least 36 hours, or at least 48 hours. This can be observed, for example, when the active agent continues to be released into the bloodstream up to 24 hours, or longer, after skin wash.

In some embodiments, the compositions described herein also advantageously achieve a high level of active agent delivery over a large range of active agent concentrations. In addition, in some embodiments, the compositions are formulated to promote reproducibility of absorption levels between different applications and between different patients.

Thus, in accordance with some embodiments, there are provided sustained release transdermal pharmaceutical compositions for topical administration to a skin surface comprising a pharmaceutically active agent and a fatty acid ester, wherein the weight:weight ratio of the fatty acid ester in the composition to the active agent in the composition is at least 4:1 fatty acid ester:active agent, such as ranging from 4:1 to 20:1. In some embodiments, the composition further comprises water, an alcohol and a fatty acid. In some embodiments, the composition even further comprises a co-solvent, such as propylene glycol. Other conventional components for transdermal pharmaceutical compositions may also be included, as discussed in more detail below.

In particular, as discussed in more detail in the examples below, the compositions described herein relate to the unexpected discovery that providing a fatty acid ester in at least a four-fold excess over the therapeutically active agent (on a w/w basis) results in a transdermal pharmaceutical composition with advantageous properties, including sustained release, consistent delivery profiles over a range of active agent concentrations, and application-to-application and patient-to-patient reproducibility. While not wanting to be bound by any theory, it is believed that this high fatty acid ester to active agent ratio facilitates partitioning of the active agent into the dermis and formation of a depot within the dermis, resulting in dermal retention of the active agent followed by sustained release into the bloodstream. Hence, the compositions and methods described herein also provide a method for increasing dermal retention of an active agent, and achieving sustained release delivery.

Thus, in accordance with some embodiments, there is provided a method for providing a sustained release of a pharmaceutically active agent through the skin of a subject, comprising topically administering to the skin of the subject a pharmaceutical composition comprising a therapeutically effective amount of the active agent and a fatty acid ester, wherein the weight:weight ratio of the fatty acid ester in the composition to the active agent in the composition is at least 4:1 fatty acid ester:active agent. In some embodiments, the composition further comprises water, an alcohol and a fatty acid. In some embodiments, the composition even further comprises a co-solvent, such as propylene glycol. Other conventional components for transdermal pharmaceutical compositions may also be included, as discussed in more detail below.

As used herein, the phrase "sustained" delivery means that the compositions continue to deliver the active agent over a period of time of at least 12 hours, at least 24 hours, at least 36 hours, or at least 48 hours, including a period of time of at least 24 hours. For example, sustained delivery compositions may continue to deliver the active agent after the first 24 hours after application. In some embodiments, sustained delivery compositions described herein continue to deliver a therapeutically effective amount of the active agent after the first 24 hours after application. Depending on the composition and the active agent, this may constitute the delivery after the first 24 hours of, for example, at least 5%, at least 10%, at least 15%, at least 20%, at least 25%, at least 30%, or more, of the total amount of active agent delivered. Again depending on the composition and the active agent, this may constitute the delivery after the first 24 hours of, for example, at least 2%, at least 3%, at least 4%, at least 5%, or more, of the total amount of active agent applied in the composition. This can be observed, for example, when the active agent continues to be released into the bloodstream up to 24 hours, or longer, after application.

In some embodiments, sustained delivery compositions described herein continue to deliver active agent after the first 12, 24, 36, or 48 hours after application, at a level that is greater than the amount delivered during the same time period by a comparable composition that does not include a fatty acid ester. As illustrated in Example 2, this can be observed by, for example, testing a composition as described herein and a comparable composition that does not include a fatty acid ester (e.g., a composition that is identical except for the absence of fatty acid ester) in an in vitro Franz cell assay, where the compositions are applied to a skin sample in the Franz cell, left for 24 hours, and then washed off, and then drug delivery through the skin after washing (e.g., after the first 24 hours after application) is determined and compared.

The compositions and methods are described in more detail below, and illustrated in the examples.

As used herein, and unless otherwise specified, "a" or "an" means "one or more."

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

Pharmaceutical Compositions

As noted above, described herein are compositions comprising a therapeutically effective amount of a therapeutically active agent and a fatty acid ester, wherein the weight:weight ratio of the fatty acid ester in the composition to the active agent in the composition is at least 4:1 fatty acid ester:active agent, such as ranging from 4:1 to 20:1. In particular embodiments, the compositions comprise a pharmaceutically active agent, a fatty acid ester, water, an alcohol and a fatty acid.

In further particular embodiments, the composition further comprises a co-solvent, such as propylene glycol.

In specific embodiments, the composition comprises about 2% fatty acid (such as oleic acid), about 2% fatty acid ester (such as ethyl oleate), and about 5% co-solvent (such as propylene glycol). In further specific embodiments, the composition comprises 2% fatty acid (such as oleic acid), 2% fatty acid ester (such as ethyl oleate), and 5% co-solvent (such as propylene glycol). In other specific embodiments, the composition comprises about 0.3% fatty acid (such as oleic acid), about 0.3% fatty acid ester (such as ethyl oleate), and about 0.75% co-solvent (such as propylene glycol). In further specific embodiments, the composition comprises 0.3% fatty acid (such as oleic acid), 0.3% fatty acid ester (such as ethyl oleate), and 0.75% co-solvent (such as propylene glycol). As noted above, as used herein, the term "about" embraces plus or minus 10% of the listed amounts.

In some embodiments, the composition comprises the specified components. In some embodiments, the composition consists of the specified components. In other embodiments, the composition consists essentially of the specified components. As used herein, "consists essentially of" the specified components means that the composition includes at least the specified components, and may also include other components that do not materially affect the basic and novel characteristics of the invention.

Specific components of the compositions are described in detail below.

Active Agents

The compositions described herein include at least one therapeutically active agent. In some embodiments, the active agent is a drug molecule of generally hydrophobic nature, with a small size, such as a molecular weight below 500 Dalton. In some embodiments, the active agent is selected from steroids, including hormones and sex hormones. The term "sex hormone" refers to natural or synthetic steroid hormones that interact with vertebrate androgen or estrogen receptors, such as estrogens, anti-oestrogens (or SERMs), androgens, anti-androgens, progestins, and mixtures thereof. When the composition comprises more than one steroid, the weight:weight ratio of the fatty acid ester in the composition to the total amount of steroid in the composition is at least 4:1 fatty acid ester:steroids, such as ranging from 4:1 to 20:1.

In some embodiments where the composition comprises one or more steroids and one or more other therapeutically active agents, the weight:weight ratio of the fatty acid ester in the composition to the total amount of active agents in the composition is at least 4:1 fatty acid ester:active agents. In other embodiments, the weight weight ratio of the fatty acid ester in the composition to the total amount of active agents in the composition is less than 4:1 fatty acid ester:active agent, although the weight:weight ratio of the fatty acid ester in the composition to the total amount of steroid in the composition is at least 4:1 fatty acid ester:steroid.

For example, steroid hormones suitable for use in the compositions described herein include the numerous natural and synthetic steroid hormones, including androgens, estrogens, and progestagens and derivatives thereof, such as dehydroepiandrosterone (DHEA), androstenedione, androstenediol, dihydrotestosterone, testosterone, progesterone, progestins, oestriol, oestradiol. Other suitable steroid hormones include glucocorticoids, thyroid hormone, calciferol, pregnenolone, aldosterone, cortisol, and derivatives thereof. Suitable steroid hormones especially include the sexual hormones having estrogenic, progestational, androgenic, or anabolic effects, such as estrogen, estradiol and their esters, e.g., the valerate, benzoate, or undecylate, ethinylestradiol, etc.; progestogens, such as norethisterone acetate, levonorgestrel, chlormadinone acetate, cyproterone acetate, desogestrel, or gestodene, etc.; androgens, such as testosterone and its esters (propionate, undecylate, etc.), etc.; anabolics, such as methandrostenolone, nandrolone and its esters.

Estrogens

In specific embodiments, the one or more estrogen(s) are selected from the group consisting of natural oestrogens, such as 17β-oestradiol, oestrone, equine conjugated oestrogens, estriol and phytoestrogens; semi-natural oestrogens, such as oestradiol valerate; or synthetic oestrogens, such as ethinyl-estradiol.

In some embodiments, a pharmaceutical composition is provided for topical administration to a skin surface comprising water, at least one therapeutically active agent selected from the estrogens, an alcohol, and a fatty acid ester. In some embodiments, a pharmaceutical composition is provided for topical administration to a skin surface comprising water, at least one therapeutically active agent being estradiol, an alcohol, and a fatty acid ester. In particular embodiments of such compositions when the active agent is estradiol, the composition does not further comprise the combination of progesterone, propylene glycol, oleic acid, ethyl oleate, ethanol, hydroxypropylcellulose and purified water.

Anti-Estrogens

Anti-estrogens are a class of pharmaceutically active agents now referred to as Selective Estrogen Receptors Modulators (SERMs), which were generally understood to be compounds capable of blocking the effect of estradiol without displaying any estrogenic activity of their own. Such a description is now known to be incomplete, however. The term SERM has been coined to describe compounds that, in contrast to pure estrogen agonists or antagonists, have a mixed and selective pattern of estrogen agonist-antagonist activity, which largely depends on the targeted tissue. The pharmacological goal of these drugs is to produce estrogenic actions in those tissues where these actions are beneficial (such as bone, brain, liver) and to have either no activity or antagonistic activity in tissues such as breast and endometrium, where estrogenic actions (cellular proliferation) might be deleterious.

In specific embodiments, the anti-estrogens (SERMs) are selected from the group consisting of endoxifen, droloxifene, clomifene, raloxifene, tamoxifen, 4-OH tamoxifen, toremifene, danazol, and pharmaceutically acceptable salts thereof. In a more particular embodiment, a pharmaceutical composition is provided for topical administration to a skin surface comprising water, at least one therapeutically active agent selected from the anti-oestrogens (SERMs) selected from the group consisting of clomifene, raloxifene, droloxifene, endoxifen or the pharmaceutically acceptable salts thereof, an alcohol, and a fatty acid ester.

In a particular embodiment, a pharmaceutical composition is provided for topical administration to a skin surface comprising water, at least one therapeutically active agent selected from the anti-estrogens (SERMs), an alcohol, and a fatty acid ester. In some particular embodiments of such compositions, when the active agent is tamoxifen, the fatty acid ester is not isopropyl myristate. In other particular embodiments of such compositions, when the active agent is tamoxifen, the composition further comprises a fatty acid. In yet other particular embodiments of such compositions, when the active agent is 4-OH tamoxifen, the fatty acid ester is not isopropyl myristate. In other particular embodiments of such compositions, when the active agent is 4-OH tamoxifen, the composition further comprises a fatty acid.

Androgens

In some embodiments, androgens may be selected from the group consisting of the natural androgen, testosterone, and its semi-natural or synthetic derivatives, for instance methyltestosterone; physiological precursors of testosterone such as dehydroepiandrosterone or DHEA, or alternatively prasterone and its derivatives, for instance DHEA sulphate, Δ-4-androstenedione and its derivatives; testosterone metabolites, for instance dihydrotestosterone (DHT) obtained after the enzymatic action of 5-α-reductases; or substances with an androgenic-type effect, such as tibolone.

In a particular embodiment, a pharmaceutical composition is provided for topical administration to a skin surface comprising water, at least an active agent selected from the androgens, an alcohol, and a fatty acid ester. In particular embodiments of such compositions, when the active agent is testosterone or dihydrotestosterone (DHT), the composition also comprises a fatty acid as a penetration enhancer.

Anti-Androgens

In some embodiments, the anti-androgens are selected from the group consisting of steroidal compounds such as cyproterone acetate and medroxyprogesterone, or non-steroidal compounds such as flutamide, nilutamide or bicalutamide.

In a particular embodiment, a pharmaceutical composition is provided for topical administration to a skin surface comprising water, at least one active agent selected from the anti-androgens, an alcohol, and a fatty acid ester.

Progestins

In some embodiments, the progestin(s) used in the pharmaceutical compositions described herein may be selected from the group consisting of natural progestins, progesterone or its derivatives of ester type, and synthetic progestins of type 1, 2 or 3.

The first group comprises molecules similar to progesterone or the synthetic progestins 1 (SP1) (pregnanes), for example the progesterone isomer (retroprogesterone), medrogesterone, and norprogesterone derivatives (demegestone or promegestone).

The second group comprises 17α-hydroxy-progesterone derivatives or synthetic progestins 2 (SP2) (pregnanes), for example cyproterone acetate and medroxyprogesterone acetate.

The third group comprises norsteroids or synthetic progestins 3 (SP3), (estranes or nor-androstanes). These are 19-nortestosterone derivatives, for example norethindrone. This group also comprises molecules of gonane type, which are derived from these nor-androstanes or estranes and have a methyl group at C18 and an ethyl group at C13. Examples that may be mentioned include norgestimate, desogestrel (3-ketodesogestrel) or gestodene. Tibolone, which has both progestin and androgenic activity, may also advantageously be selected in the pharmaceutical composition described herein.

In a particular embodiment, a pharmaceutical composition is provided for topical administration to a skin surface comprising water, at least one therapeutically active agent selected from the progestins, an alcohol, and a fatty acid ester. In particular embodiments of such compositions, when the active agent is progesterone, the composition does not further comprise the combination of estradiol, propylene glycol, oleic acid, ethyl oleate, ethanol, hydroxypropylcellulose and purified water.

In particular embodiments, the therapeutically active agent in the pharmaceutical composition is a progestin, an estrogen or a combination of the two.

As noted above, when the composition comprises more than one steroid, the weight:weight ratio of the fatty acid ester in the composition to the total amount of steroid active agent in the composition is at least 4:1 fatty acid ester:active agent, such as ranging from 4:1 to 20:1.

The amount of therapeutically active agent present in the composition generally will be influenced by the dosage to be delivered for therapeutic effect and formulary considerations. The compositions generally include a therapeutically effective amount of active agent. As used herein, the phrase "therapeutically effective amount" means an amount (dosage) that achieves in a subject the specific pharmacological response for which the drug is administered. It is emphasized that a "therapeutically effective amount" of a drug that is administered to a particular subject in a particular instance may not always be effective in treating the target conditions/diseases, even though such dosage is deemed to be a therapeutically effective amount by those of skill in the art. Those skilled in the art will recognize that the "therapeutically effective amount" may vary from patient to patient, or from condition to condition, and can determine a "therapeutically effective amount" for a given patient/condition by routine means.

The therapeutically active agent is advantageously present in the composition in an amount ranging from about 0.01% to about 5%, or from 0.01% to 5%, including from about 0.02% to about 3%, or from 0.02% to 3%, such as from about 0.03% to about 2%, or from 0.03% to 2%, including from about 0.05% to about 0.5%, or from 0.05% to 0.5%, such as from about 0.2% to about 0.4%, or from 0.2% to 0.4%, these percentages being expressed by weight, relative to the total weight of the pharmaceutical composition.

According to one embodiment, when the active agent comprises a progestin, the progestin content ranges from about 0.01% to about 5%, including from about 0.05% to about 3%, such as from about 0.1% to about 1%, these percentages being expressed by weight, relative to the total weight of the pharmaceutical composition. Thus, in some embodiments, the progestin content may range from 0.01% to 5%, including from 0.05% to 3% such as from 0.1% to 1%, According to another embodiment, when the active agent comprises an estrogen, the estrogen content ranges from about 0.01% to about 5%, including from about 0.02% to about 3%, such as from about 0.03% to about 2%, including from about 0.05% to about 0.50%, such as from about 0.20% to about 0.40%, these percentages being expressed by weight, relative to the total weight of the pharmaceutical composition. Thus, in some embodiments, the estrogen content may range from 0.01% to 5%, including from 0.02% to 3%, such as from 0.03% to 2%, including from 0.05% to 0.50%, such as from 0.20% to 0.40%, including from about 0.30% to 0.40%.

In one embodiment, when the active agent comprises an estrogen, the estrogen content will range from about 0.30% to 0.40%.

Fatty Acid Ester

The compositions described herein comprise at least one fatty acid ester. The fatty acid esters suitable for use herein include long-chain aliphatic fatty acid esters containing from 8 to 22 carbon atoms, such as from 12 to 20 carbon atoms.

The fatty acid esters may be those that would result from the reaction of an alcohol with a fatty acid selected, in a non-limiting manner, from the group consisting of capric acid (10:0), lauric acid (12:0), myristic acid (14:0), palmitic acid (16:0), stearic acid (18:0), oleic acid (18:1), isostearic acid (18:0), palmitoleic acid (16:1), linoleic acid (18:2) and linolenic acid (18:3).

Thus, for example, the fatty acid ester can optionally be selected from the group consisting of ethyl oleate, isopropyl oleate, isopropyl myristate, isopropyl isostearate, isopropyl palmitate, ethyl octanoate, ethyl dodecanoate, ethyl linoleate, ethyl palmitoleate, ethyl isostearate and ethyl linolenate. In a particular embodiment, the fatty acid ester is an ester that would result from the reaction of an alcohol with oleic acid.

In one embodiment, the fatty acid ester is an ester that would result from the reaction of the fatty acid formulated in the composition with an alcohol. In other embodiments, the fatty acid ester is not an ester that would result from the reaction of the fatty acid formulated in the composition with an alcohol. In one embodiment, the fatty acid ester is not the ester that would result from the reaction of the fatty acid formulated in the composition with the alcohol formulated in the composition. For example, in the context of the disclosed compositions, the advantageous results discussed herein, such as sustained delivery believed to be due to formation of a depot in the dermis, may be observed without regard to whether the fatty acid ester formulated in the composition corresponds to any fatty acid also formulated in the composition.

As noted above, that fatty acid ester is present in the composition in at least a four-fold excess over the therapeutically active agent (on a w/w basis), i.e., the weight:weight ratio of the fatty acid ester present in the composition to the active agent present in the composition is at least 4:1 fatty acid ester:active agent. Thus, in some embodiments, the weight:weight ratio of the fatty acid ester:active agent ranges from 4:1 to 20:1. In another embodiment, the weight:weight ratio of the fatty acid ester present in the composition to the active agent present in the composition ranges from 4:1 to 15:1; in further embodiments, the ranges is from 5:1 to 10:1, or from 5:1 to 7:1. Within these parameters, the fatty acid ester content in the pharmaceutical composition may range from about 0.1% to about 20% by weight, such as from about 0.2% to about 10% by weight, including from about 0.5% to about 5% by weight, all based on the total weight of the pharmaceutical composition. Thus, the compositions may comprise fatty acid ester in an amount from 0.10% to 20% by weight, such as from 0.2% to 10% by weight, including from 0.5% to 5% by weight.

In particular embodiments, the fatty acid ester content in the pharmaceutical composition may range from about 0.01% to about 5%, including from about 0.05% to about 2.4%, such as from about 0.1% to about 2.2%, these percentages being expressed by weight, relative to the total weight of the pharmaceutical composition. Thus, the fatty acid ester content may range from 0.01% to 5%, including from 0.05% to 2.4%, such as from 0.1% to 2.2%, Fatty Acid In some embodiments, the composition may comprise at least one fatty acid that can either be saturated or unsaturated, such as a fatty acid penetration enhancer.

Exemplary fatty acids suitable for use include long-chain aliphatic fatty acids containing from 8 to 22 carbon atoms, such as from 10 to 18 carbon atoms. The fatty acids may be selected, in a non-limiting manner, from the group consisting of capric acid (10:0), lauric acid (12:0), myristic acid (14:0), palmitic acid (16:0), stearic acid (18:0); oleic acid (18:1), isostearic acid (18:0), palmitoleic acid (16:1), linoleic acid (18:2) and linolenic acid (18:3). In a particular embodiment, the fatty acid is oleic acid.

In a particular embodiment, the fatty acid formulated in the composition corresponds to the fatty acid ester also formulated in the composition, such as a composition comprising ethyl oleate and oleic acid. Thus, in a particular embodiment, the composition comprises both oleic acid and at least one of its corresponding esters. In other embodiments, the fatty acid formulated in the composition does not correspond to the fatty acid ester also formulated in the composition.

The fatty acid content in the pharmaceutical composition described herein will advantageously range from about 0.01% to about 5%, including from about 0.05% to about 3.5%, such as from about 1% to about 3%, these percentages being expressed by weight, relative to the total weight of the pharmaceutical composition. Thus, in some embodiments, the fatty acid content may range from 0.01% to 5%, including from 0.05% to 3.5%, such as from 1% to 3%, Alcohol As noted above, the compositions described herein comprise at least one alcohol. As used herein the term "alcohol" refers to an organic molecule containing at least one carbon atom and only one alcohol group —OH (monoalcohol).

Exemplary alcohols are C2-C6 alcohols and can include C2-C4 alcohols, such as ethanol, n-propanol, isopropanol, n-butanol, isobutanol, tert-butanol, or mixtures thereof. Exemplary, non-limiting alcohols suitable for use in the compositions are ethanol and isopropanol.

The presence of such an alcohol may also accelerate drying of the composition onto the skin. For that reason, alcohols may be chosen that have a boiling point in the range of about 70 to about 130° C., including in the range of about 75 to about 85° C.

Typically, the alcohol will be used in an amount ranging from about 10% to about 90%, including from about 20% to about 80%, such as from about 45% to about 75%, these percentages being expressed by weight, relative to the total weight of the pharmaceutical composition. Thus, in some embodiments, the alcohol may be present in an amount ranging from 10% to 90%, including from 20% to 80%, such as from 45% to 75%.

Co-Solvent

The pharmaceutical composition described herein may also comprise a co-solvent. Co-solvents suitable for use in pharmaceutical compositions are known in the art, such as polyols or polyglycols. In some embodiments, one or more co-solvents are selected from the group consisting of glycerol, propylene glycol and polyethylene glycol.

The co-solvent may be present in the composition in an amount ranging from about 0.01% to about 7%, including from about 3% to about 7%, such as from about 4% to about 6%, these percentages being expressed by weight, relative to the total weight of the pharmaceutical composition. Thus, in some embodiments, the co-solvent may be present in an amount ranging from 0.01% to 7%, including from 3% to 7%, such as from 4% to 6%.

The co-solvent generally increases the solubility of the therapeutically active agent(s) and in particular may contribute to maintain in solution the therapeutically active agent remaining on the skin surface once the alcohol has dried. For that reason, co-solvents may be selected that have a boiling point in the range of about 150° C. to about 300° C., such as in the range of about 150° C. to about 200° C.

Gelling Agents

The compositions may optionally comprise at least one gelling agent.

As used herein, the term "gelling agent" specifies a compound, optionally of polymeric nature, having the capacity to form a gel when contacted with a specific solvent, e.g., water. Gelling agents (e.g., thickeners) suitable for use in pharmaceutical compositions are known in the art. Gelling agents may act to increase the viscosity of the pharmaceutical compositions. For example, a gelling agent may provide the composition with sufficient viscosity to allow easy application of the composition onto the skin. Additionally or alternatively, gelling agents may act as solubilizing agents.

Examples of gelling agents include anionic polymers such as acrylic acid based polymers (including polyacrylic acid polymers, e.g. CARBOPOL® by Noveon, Ohio), cellulose derivatives, poloxamers and poloxamines, more precisely, Carbomers which are acrylic acid-based polymers, e.g. CARBOPOL® 980 or 940, 981 or 941, 1342 or 1382, 5984, 934 or 934P (CARBOPOL® are usually polymers of acrylic acid crosslinked with allyl sucrose or allylpentaerythritol), Ultrez, PEMULEN® TR 1 or TR 2 commercialized by Lubrizol (high molecular weight copolymer of acrylic acid and C10-C30 alkyl acrylate crosslinked with allyl pentaerythritol), Synthalen CR, etc.; cellulose derivatives such as carboxymethylcelluloses, hydroxypropylcelluloses (KLUCEL®, for example KLUCEL® HF or KLUCEL® HPC sold by Hercules Incorporated), hydroxyethylcelluloses, ethylcelluloses, hydroxymethylcelluloses, hydroxypropylmethylcelluloses, and the like, and mixtures thereof; poloxamers or polyethylene-polypropylene copolymers such as LUTROL® grade 68 or 127, poloxamines and other gelling agents such as chitosan, dextran, pectins, and natural gums. Any one or more of these gelling agents may be used alone or in combination in the pharmaceutical compositions described herein. In one aspect, the gelling agent is selected from the group consisting of polyacrylic acids, cellulosics, and mixtures thereof.

In one embodiment, the compositions described herein comprise PEMULEN® as a gelling agent.

Typically, the gelling agent will be used in an amount ranging from about 0.05% to about 5% by weight, including about 0.1% to about 3%, such as from about 1.5% to about 2.5% by weight, these percentages being expressed by weight, relative to the total weight of the pharmaceutical composition. Thus, the gelling agent may be present in an amount ranging from 0.05% to 5% by weight, including 0.1% to 3%, such as from 1.5% to 2.5% by weight.

Moisturizers

The compositions may optionally comprise at least one moisturizer.

As used herein "moisturizer" specifies an agent that hydrates the skin. Moisturizers suitable for use in pharmaceutical compositions are known in the art. Moisturizers can be used either alone or in combination, e.g., a combination of two or three (or more) different moisturizers can be used. In some embodiments, moisturizers are selected from emollients and/or humectants.

As used herein, "emollients" specify substances that soften the skin and tend to improve moisturization of the skin. Emollients suitable for use in pharmaceutical compositions are well known in the art, and include mineral oil, petrolatum, polydecene, isohexadecane, fatty acids and alcohols having from 10 to 30 carbon atoms; pelargonic, lauric, myristic, palmitic, stearic, isostearic, hydroxystearic, oleic, linoleic, ricinoleic, arachidic, behenic, and euricic acids and alcohols; triglyceride esters, castor oil, cocoa butter, safflower oil, sunflower oil, jojoba oil, cottonseed oil, corn oil, olive oil, cod liver oil, almond oil, avocado oil, palm oil, sesame oil, squalene, Kikui oil, soybean oil, acetoglyceride esters, ethoxylated glycerides, ethoxylated glyceryl monostearate, alkyl esters of fatty acids having 10 to 20 carbon atoms, hexyl laurate, isohexyl laurate, isohexyl palmitate, isopropyl palmitate, decyl oleate, isodecyl oleate, hexadecyl stearate, decyl stearate, diisopropyl adipate, diihexyl adipate, diisopropyl sebacate, laurly lactate, myristyl lactate, acetyl lactate; alkenyl esters of fatty acids having 10 to 20 carbon atoms, oleyl myristate, oleyl stearate, oleyl oleate, fatty acid esters of ethoxylated fatty alcohols, polyhydric alcohol esters, ethylene glycol mono and di-fatty acid esters, diethylene glycol mono- and di-fatty acid esters, polyethylene glycol, wax esters, beeswax, spermaceti, myristyl myristate, stearyl stearate, silicone oils, dimethicones, cyclomethicones. In some embodiments, the composition comprises one or more emollients that are liquid at room temperature.

As used herein "humectants" specifies hygroscopic substances that absorb water from the air. Exemplary humectants suitable for use include glycerine, propylene glycol, glyceryl triacetate, a polyol, sorbitol, maltitol, a polymeric polyol, polydextrose, *quillaia*, lactic acid, and urea.

Exemplary moisturizers suitable for use may comprise amines, alcohols, glycols, amides, sulfoxides, and pyrrolidones. In one aspect, the moisturizer is selected from the group consisting of lactic acid, glycerine, propylene glycol, and urea.

In one embodiment, the moisturizer is used in an amount ranging from about 0.01% to about 30% by weight, including from about 0.05% to about 20% by weight, such as from about 0.1% to about 10% by weight, including from about 0.5% to about 5% by weight, these percentages being expressed by weight, relative to the total weight of the pharmaceutical composition. Thus, for example, a moisturizer may be used in an amount ranging from 0.01% to 30% by weight, including from 0.05% to 20% by weight, such as from 0.1% to 10% by weight, including from 0.5% to 5% by weight.

In one embodiment, the composition comprises glycerin in an amount ranging from about 0.01% to about 30% by weight, including from about 0.05% to about 20% by weight, such as from about 0.1% to about 10% by weight, including from about 0.5% to about 5% by weight, these percentages being expressed by weight, relative to the total weight of the pharmaceutical composition. Thus, in some embodiments, a composition may comprise glycerin in an amount ranging from 0.01% to 30% by weight, including from 0.05% to 20% by weight, such as from 0.1% to 10% by weight, including from 0.5% to 5% by weight.

Aqueous Vehicle

As noted above, the composition described herein comprises an aqueous vehicle, and thus includes water. Aqueous vehicles suitable for pharmaceutical compositions are known in the art.

According to one embodiment, the aqueous vehicle comprises, besides water, ingredients useful in adjusting the pH, for instance at least one buffering agent, which advantageously makes it possible to maintain the pH of the composition between about 4 and about 10, such as between about 5 and about 9, or between about 6 and about 8, including from 4 to 10, from 5 to 9 and from 6 to 8.

According to another embodiment of the pharmaceutical composition, the buffers are selected from the group consisting of:

basifying or basic buffers such as a phosphate buffer (for example dibasic or monobasic sodium phosphate), a citrate buffer (for example sodium citrate or potassium citrate), sodium carbonate, sodium bicarbonate, including a mixture of sodium carbonate and sodium bicarbonate, or neutral buffers such as a Tris buffer (for example tris maleate), or a phosphate buffer.

In one embodiment, the compositions comprise a mixture of sodium carbonate and sodium bicarbonate.

The buffer can be introduced in the composition either directly, for example added in a powdery form, or diluted in water, for example to a concentration ranging from 1 to 500 mM. Thus, additionally or alternatively, the liquid buffer solution can be introduced in the composition.

The skilled artisan would understand how to adjust the amount of buffer to obtain the desired buffering effect, depending on the chemical nature of the buffer used, its form (either powdery or diluted in water) and the starting and desired pH of the composition.

Without being limited to these values, it can reasonably be estimated that when the buffers used in the composition are a mixture of sodium carbonate and sodium bicarbonate introduced in a powdery form (see example 8 of the present application), sodium carbonate can be introduced in an amount ranging from about 0.01 to 0.1%, and sodium bicarbonate can be introduced in an amount ranging from about 0.001 to 0.01%, these percentages being expressed by weight, relative to the total weight of the pharmaceutical composition.

Without being limited to these values, it can reasonably be estimated that when the buffer used in the composition is a 60 mM solution of carbonate buffer having a pH=10.7 (see examples 1 to 3 of the present application), the 60 mM buffer solution can be introduced in an amount ranging from about 1% to about 80%, including from about 5% to about 70%, such as from about 10% to about 50%, these percentages being expressed by weight, relative to the total weight of the pharmaceutical composition.

However, the amount of buffer in the composition can further vary depending on the composition of the formula in which it is introduced, in accordance with standard buffering techniques.

In another aspect, the pharmaceutical compositions described herein further comprises a base. Advantageously, the base is, for example, pharmaceutically acceptable, and is typically selected from the group consisting of triethanolamine, sodium hydroxide, ammonium hydroxide, potassium hydroxide, arginine, aminomethylpropanol or tromethamine, and mixtures thereof. Where the pH of the pharmaceutical composition is not optimized for transdermal administration, e.g., where the gelling agent comprises at least one acrylic acid-based polymer resulting in a pH more acidic than desired for the final product, the use of a base may contribute to the neutralization of the pharmaceutical composition. Furthermore, the use of the base (neutralizer) may improve or optimize swelling of the polymer chains during the neutralization of the charges and the formation of polymer salts. In embodiments where the gelling agent comprises an acrylic acid-based polymer, the base may comprise triethanolamine. The use of a base also may improve or optimize viscosity.

The skilled person will know how to choose a suitable amount of base for use in the composition, and may select the base based on the nature of the gelling agent present therein, and the alcohol content of the composition. For example, with carbomers and/or a high alcohol content, tromethamine and/or NaOH may be selected as a base, in amounts chosen so as to reach the desired final pH in the composition.

Further Optional Components

The pharmaceutical compositions described herein optionally may comprise other usual pharmaceutical additives, including salt(s), stabilizer(s), antimicrobial(s) such as paraben compounds, fragrance(s), and/or propellant(s).

In some embodiments, it may for example be advantageous to include a stabilizer such as butylated hydroxyanysol (BHA), butylated hydroxytoluene (BHT) and ascorbic acid. BHA, however, may color the compositions in yellow. Therefore, in another embodiment, the composition does not comprise BHA.

Depending on the nature of the selected ingredients, it may be advantageous to include a surfactant. Surfactants suitable for use in pharmaceutical compositions are known in the art, and the skilled person can select suitable surfactants for use in the compositions described herein, such as surfactants that are dermatologically and/or cosmetically acceptable. Examples thereof include non-ionic surfactants, for example:

esters, such as:
esters of polyethyleneglycol with fatty acids, including LABRASOL®, which is a mixture of mono-, di- and triglycerides and of mono- and diesters of polyethyleneglycol with fatty acids;
esters of saccharose with fatty acids, such as sucrose laurate with HLB 16; sucrose palmitate with HLB 16;
esters of sorbitanne polyoxyethylene, such as TWEEN® compounds including TWEEN® 20, 60 and/or 80;
alkylene oxide copolymers, such as copolymers of ethylene oxide and propylene oxide, e.g. PLURONICS®.

Further examples include anionic surfactants such as SDS (sodium dodecyl sulphate), and the like and cationic surfactants such as cetrimide (alkyltrimethylammonium bromide) and the like.

Typically, surfactants will be used in the compositions in an amount ranging from about 0.01% to about 5% by weight, including about 0.05% to about 3% by weight, these percentages being expressed by weight, relative to the total weight of the pharmaceutical composition. Thus, in some embodiments, a surfactant may be used in the compositions in an amount ranging from 0.01% to 5% by weight, including 0.05% to 3% by weight.

The pharmaceutical composition described herein may be in the form of a solution, a gel, a cream, a lotion, a milk, an ointment, an aerosol or a patch.

In one embodiment, the composition is in the form of a gel or a solution.

Exemplary Composition and Uses

Exemplary, non-limiting compositions are provided below. As mentioned above, percentages (%) refer to amounts by weight based upon the total weight of the composition (w/w). The sum of the different components of the composition adds up to 100% (w/w) of the total composition.

In one aspect, a pharmaceutical composition is provided for topical administration to a skin surface wherein the composition comprises:

(i) 0.01 to 2.5% (w/w) of a pharmaceutically active agent comprising one or more steroids,
(ii) 10 to 90% (w/w) of at least one C2-C6 monoalcohol, such as ethanol or isopropanol,
(iii) 0.04 to 10% (w/w) of a fatty acid ester,
(iv) 0 to 10% (w/w) of a fatty acid
(v) 0 to 5% (w/w) of at least one gelling agent, (vi) q.s.f. 100% (w/w) water, wherein the weight:weight ratio of the fatty acid ester in the composition to the total active agent in said composition is at least 4:1 fatty acid ester:active agent.

In one embodiment, a pharmaceutical composition is provided for topical administration to a skin surface wherein the composition comprises:
(i) 0.01 to 1.25% (w/w), such as 0.30 to 0.50% (w/w), of a pharmaceutically active agent chosen from estrogens, such as estradiol,
(ii) 20 to 80% (w/w) of at least one a C2-C6 monoalcohol, such as ethanol or isopropanol,
(iii) 0.04 to 5% (w/w) of a fatty acid ester, such as ethyl oleate
(iv) 0.01 to 5% (w/w) of a fatty acid, such as oleic acid,
(v) 0.05% to 5% (w/w) of at least one gelling agent, such as a high molecular weight copolymer of acrylic acid and C10-C30 alkyl acrylate crosslinked with allyl pentaerythritol, for example PEMULEN® TR-1,
(vi) q.s.f. 100% (w/w) water,
wherein the weight:weight ratio of the fatty acid ester in the composition to the total active agent in said composition is at least 4:1 fatty acid ester:active agent, such as ranging from 4:1 and 7:1.

Depending on the active agent used, the pharmaceutical compositions described herein can be useful for various treatments. For example, the compositions can be used in any methods where the delivery of a pharmaceutically active agent is desired, and may be particularly useful where sustained, systemic delivery of the pharmaceutically active agent is desired. When the composition comprises one or more steroids, it can be used in any method where the delivery of the steroid(s) is desired, and may be particularly useful where sustained, systemic delivery of the steroid(s) is desired. For example, the compositions can be used in methods to treat a patient suffering from or at risk of developing any condition that may be treated, ameliorated or prevented by the systemic administration of one or more steroids, Exemplary, non-limiting therapeutic methods include:

When the active agent is an antiestrogen (SERM), compositions described herein are useful for treating a patient suffering from or at risk of developing a breast disorder such as:
conditions involving dense breast tissue, such as high density breast tissue that is a predictor of breast cancer risk and/or that compromises mammographic sensitivity;
benign breast diseases, such as adenosis, cysts, duct ectasia, fibroadenoma, fibrosis, hyperplasia, metaplasia and other fibrocystic changes;
gynecomastia;
breast cancer, including non-invasive breast cancer;
malignant melanoma;
mastalgia;
localized cancer and/or tumours such as lung tumours; and
other therapies involving the systemic administration of an antiestrogen.

When the active agent is an estrogen such as estradiol, an antiestrogen (SERM), an androgen such as testosterone or DHT, compositions described herein are useful for treating a bone-related disorder such as osteoporosis, menopause-associated osteoporosis, glucocorticoid-induced osteoporosis, Paget's disease, abnormal bone resorption, bone cancer, bone loss (generalized bone loss and/or localized bone loss), bone metastasis (with or without hypercalcemia), multiple myeloma and other conditions that feature bone fragility.

When the active agent is an estrogen such as estradiol, compositions described herein are useful for
the prevention of cardiovascular diseases or improvement of cognitive functions;
managing symptoms of menopause, such as hot flashes, night sweats, sleeping problems (insomnia), fatigue, vaginal dryness and itching and burning, loss of sexual desire, irregular periods, bladder problems, and mood swings;
prostate cancer; and
other therapies involving the systemic administration of an estrogen.

When the active agent is a progestogen such as progesterone, compositions described herein are useful for treating
begnin breast disease, mastodynia, mastopathy, cyclical mastalgia, and to prevent cysts and begnin tumor relapse.
pre-menstrual syndrome, menstrual irregularities due to ovulation disorders or anovulation, benign mastopathy, premenopause, adjunctive use with oestrogen in post-menopausal women, prevention of endometrial hyperplasia in non-hysterectomized postmenopausal women who are receiving estrogen therapy, infertility due to lutcal phase defect, threatened abortion, and threatened preterm delivery, progesterone support during ovarian insufficiency or complete ovarian failure, in women lacking ovarian function (oocyte donation), for luteal phase support during in vitro fertilisation cycles, for luteal phase support during spontaneous or induced cycles, in primary or secondary infertility or subfertility in particular due to dysovulation; and
other therapies involving the systemic administration of a progestogen.

When the active agent is an androgen such as Testosterone or DHT, compositions described herein are useful for treating:
hypogonadism;
depressive disorder, type-2 diabetes, increasing glycemic control, erectile dysfunction, metabolic syndrome, frailty, angina pectoris, congestive cardiac failure, osteopenia and osteoporosis or treating erectile dysfunction; and
other therapies involving the systemic administration of an androgen.

While the foregoing examples have been provided, the skilled artisan readily will appreciate that the compositions described herein are useful in any context where systemic delivery of a pharmaceutically active agent, such as one or more steroids, is desired. Moreover, for any and all uses, one skilled in the art will be able to determine appropriate amounts of gel to apply daily to achieve a target in vivo delivery level using a given gel with a given active agent concentration such as by using permeation data such as that presented in FIG. 2.

Exemplary Modes of Administration

As noted above, the compositions described herein are suitable for transdermal administration. For example, the compositions can be directly applied to a surface of the skin, for direct non-occlusive transdermal/transcutaneous application. As used herein, the terms "direct"/"directly" and "non-occlusive" reflect that the compositions do not require a matrix or membrane to effect administration, and thus are not required to be dispensed via a patch, plaster, tape system, or the like. However, the compositions optionally can be dispensed via a patch, plaster, tape system or the like.

The compositions may be administered by any means effective to apply the composition to a surface of the skin. For example, the compositions may be applied manually, directly using the hand or with an applicator such as a dropper or pipette, an applicator such as a swab, brush, cloth, pad, sponge, or with any other applicator, such as a solid support comprising paper, cardboard or a laminate material, including material comprising flocked, glued or otherwise fixed fibers. Alternatively, the compositions may be applied as an aerosol or non-aerosol spray, from a pressurized or non-pressurized container. In some embodiments, the compositions are administered in metered doses, such as from a metered dose applicator or from an applicator comprising a single dose of the composition.

In some embodiments, the composition is administered to a surface of the skin over a defined surface area. The administration of a defined, finite amount of the composition to a defined surface area permits the control of the amount of active substance that is applied to a given surface area, i.e., controlling the local concentration. By controlling (e.g., limiting) local concentration, local side effects, such as local androgenic effects (including, but not limited to: acne, oily skin), can be minimized.

In some embodiments, the amount of composition administered is a defined, finite amount that provides a therapeutically effective amount (e.g., a single dose) of active agent.

Methods of Making the Compositions

Also provided herein are methods for making the pharmaceutical compositions. Those skilled in the art can prepare the pharmaceutical compositions by any suitable means, based on common general knowledge. For example, the pharmaceutically active agent(s) can be dissolved in the alcohol and mixed with the aqueous vehicle (e.g., water and other optional components discussed above) and co-solvent, if being used, followed by addition of the other excipients, such as the moisturizer if being used, and further mixing. A gelling agent, if being used, can be introduced under stirring. A neutralizer, if being used, usually is added at or near the end of the method, such as to the otherwise final composition. For example, if the composition comprises CARBOPOL®, NaOH or triethanolamine can be used to neutralize the composition. Other optional components can be added at other stages of the method, in accordance with known procedures. For example, a preservative, if being used, can be added in an appropriate solvent, at any suitable time of the process.

For example, in a particular embodiment, the components may be added and mixed in the following order:
1. Add alcohol and co-solvent and mix until uniform.
2. Slowly add therapeutically active agent and mix until completely dissolved.
3. Add fatty acid and mix until uniform.
4. Add fatty acid ester and mix until uniform.
5. Slowly add gelling agent, if being used, and mix well until completely hydrated.
6. Slowly add buffer solution, if being used, and mix until uniform.

The following specific examples are included as illustrative of the compositions described herein. These example are in no way intended to limit the scope of the invention. Other aspects of the invention will be apparent to those skilled in the art to which the invention pertains.

EXAMPLES

Example 1: In Vitro Absorption of Estradiol into the Dermis

A. Chemicals and Formulations

Tritiated estradiol [$^3$H] is used in the preparation of pharmaceutical compositions as below.

| Formulation | 1 | 2 | 3 | 4 |
|---|---|---|---|---|
| Estradiol (E2) (g) | 0.12 | 0.12 | 0.24 | 0.24 |
| Oleic acid (OA) (g) | 2 | 2 | 2 | 2 |
| ethyl oleate (EO) (g) | — | 2 | — | 2 |
| propylene glycol (PG) (g) | 5 | 5 | 5 | 5 |
| Ethanol 96% (g) | 64 | 72 | 64 | 72 |
| Carbonate buffer (CB) 60 mM, pH 10.7 Qsf (g) | 100 | 100 | 100 | 100 |

The alcohol content is adapted to solubilise the lipophilic ingredients.

B. Methods

1. Principle of the Method

Percutaneous absorption in vitro is studied quantitatively with human skin biopsies placed in Franz diffusion cells (Franz T J, "Percutaneous absorption on the relevance of in vitro data", J Invest Dermatol. 1975 March; 64(3):190-5) permitting contact of a receptor fluid with the dermis in which the absorbed substance is measured.

2. Description of the Cells

A skin biopsy is maintained horizontally between two parts of the Franz cell, delimiting two separate compartments referred to as epidermal and dermal. The epidermal compartment consists of a glass cell cap of precise surface area (1.77 cm2), placed on the upper side of the skin. The dermal compartment, on the lower side of the skin biopsies, comprises a reservoir of fixed volume (~6.5 ml) fitted with a lateral collection port. The two elements are held in place with a clamp.

The dermal compartment is filled with a receptor fluid consisting of a solution of sodium chloride at 9 g/l and bovine serum albumin at 15 g/l. This liquid is totally removed periodically throughout the assay and replaced by fresh receptor fluid using the lateral collection port.

A double water-circulation jacket, containing water at 37° C., surrounds the lower part of the cell in order to mimic physiologic skin temperature. To ensure the homogeneity of the temperature and the content in the receptor fluid, a stirring rod is placed in the dermal compartment and each cell is placed on a magnetic stirrer.

The upper part, or epidermal compartment, is open at the exterior end, exposing the surface of the skin to the ambient air of the laboratory.

3. Preparation of Skin Biopsies

The human abdominal skins used for the experiments are taken from donors following plastic surgery procedures. Skins are stored at −20° C. The day before the application of the radioactive formulations, following thawing, subcutaneous fats are removed (unless it has already been done before freezing), and the skins are dermatomed at approximately 350 Lm. The skins are mounted on the cells the day before application of the radioactive formulation.

4. Operating Procedures

Ten microliters (≈1 μCi) of the preparations are applied over the surface of the epidermis delimited by the glass cell cap. During the experiment, the receptor fluid is completely removed at 2, 4, 6, 8 and 24 hours through the lateral collection port. The dermal compartment is then refilled with fresh solution.

At the end of the test (24 hours), the residual drug remaining at the surface of the skin is removed by washing the surface. The epidermis is separated from the dermis by gently scraping with a scalpel.

5. Treatment of the Samples and Measurement of the Radioactivity

The radioactivity contained in the samples obtained as previously described is measured using a scintillating liquid beta counter equipped with dedicated software.

6. Expression of Results Obtained for the Dermis:

The quantity of estradiol which is found in the dermis is expressed in ng-equivalent-quantities or in percentages of the administered dose. Each result represents the mean value of (n) experimental determinations and is associated with its standard deviation.

7. Results and Discussion:

| No | Formulations | (n) | Quantity of Estradiol (ng) recovered into the dermis at 24 H | % of Estradiol recovered into the dermis at 24 H | Statistical Mann-Whitney test * |
|----|---|---|---|---|---|
| 1 | E2 0.12% + OA 2% + PG 5% + Ethanol 64% + CB | 15 | 704 ± 244 | 7.08 ± 2.48 | P value Form. 1/ Form. 2 = 0.0004 |
| 2 | E2 0.12% + OA 2% + EO 2% + PG 5% + Ethanol 72% + CB | 16 | 1219 ± 418 | 12.63 ± 4.33 | |
| 3 | E2 0.24% + OA 2% + PG 5% + Ethanol 64% + CB | 16 | 1557 ± 568 | 7.79 ± 2.83 | P value Form. 3/ Form. 4 = 0.003 |
| 4 | E2 0.24% + OA 2% + EO 2% + PG 5% + Ethanol 72% + CB | 17 | 2563 ± 847 | 13.07 ± 4.27 | |

* performed on the % of Estradiol recovered in the dermis at 24 h data

These results show that at both estradiol concentrations tested, the addition of ethyl oleate induces a significant increase (at least 1.5-fold) in the dermis retention of estradiol ($p<0.01$). (Compare results with Formulation 2 vs. 1 and 4 vs. 3).

Example 2: In Vitro Absorption of Testosterone into the Dermis

A. Chemicals and Formulations

Tritiated testosterone [3H] is used in the preparation of pharmaceutical compositions as below.

| Formulation | 1 | 2 |
|---|---|---|
| Testosterone (T) (g) | 0.24 | 0.24 |
| oleic acid (OA) (g) | 2 | 2 |
| ethyl oleate (EO) (g) | — | 2 |
| propylene glycol (PG) (g) | 5 | 5 |
| Ethanol 96% (g) | 64 | 72 |
| Carbonate buffer (CB) 60 mM, pH 10.7 Qsf (g) | 100 | 100 |

The alcohol content is adapted to solubilise the lipophilic ingredients.

B. Methods and results

The operating procedures disclosed in Example 1 is followed with the two testosterone formulations described above.

After 24 hours, the residual drug remaining on the surface of the skin is removed by washing cell by cell the surface of the skin just before refilling the dermal compartment with fresh receptor fluid. The cells are then monitored for another 24 h.

After 48 hours, the receptor fluid is collected and the epidermis is separated from the dermis by gently scraping with a scalpel. The dermis is separated from the lower part of the cell. The epidermis and dermis layers are digested for a few hours at 60° C. for extraction of radioactivity in 1 ml (epidermis) or in 3 ml (dermis) of SOLUENE® 350 (PACKARD).

a) Retention in Dermis at 48 h:

| No | Formulations | (n) | Quantity of Testosterone (ng) recovered into the dermis at 48 H | % of Testosterone recovered into the dermis at 48 H | Statistical Mann-Whitney test * |
|----|---|---|---|---|---|
| 1 | T 0.24% + OA 2% + PG 5% + Ethanol 64% + CB | 8 | 1308 ± 627 | 6.54 ± 3.13 | P value Form. 1/ Form. 2 = 0.046 |
| 2 | T 0.24% + OA 2% + EO 2% + PG 5% + Ethanol 72% + CB | 8 | 2069 ± 772 | 10.54 ± 3.93 | |

* performed on the % of Testosterone recovered in the dermis at 48 h data

These results show that the addition of ethyl oleate induces a significant increase (at least 1.5-fold) in dermal retention ($p<0.05$), even when measured 2 days after application and 1 day after skin washing.

b) Release into the Reservoir Between 24 h and 48 h:

| No | Formulations | (n) | Quantity of Testosterone (ng) absorbed between 24 h and 48 h | % of Testosterone absorbed between 24 h and 48 h | Statistical Mann-Whitney test * |
|----|---|---|---|---|---|
| 1 | T 0.24% + OA 2% + PG 5% + Ethanol 64% + CB | 8 | 916 ± 133 | 4.57 ± 0.67 | P value Form. 1/ Form. 2 < 0.001 |
| 2 | T 0.24% + OA 2% + EO 2% + PG 5% + Ethanol 72% + CB | 8 | 1582 ± 292 | 8.06 ± 1.49 | |

The results also show a significant impact of the ethyl oleate on the penetration absorption 24 hours after skin wash.

These results clearly show that the compositions and methods described herein provide a sustained release of testosterone active agent from the skin throughout the 24 hours after skin wash.

Example 3: In Vitro Absorption of Testosterone into the Dermis

A. Chemicals and Formulations

Tritiated testosterone [3H], is used in the preparation of pharmaceutical compositions as below.

| Formulation | 1 | 2 |
|---|---|---|
| Testosterone (T) (g) | 0.24 | 0.24 |
| myristic acid (MA) (g) | 2 | 2 |
| isopropyl myristate (IPM) (g) | — | 2 |
| propylene glycol (PG) (g) | 5 | 5 |
| isopropanol (g) | 56 | 56 |
| Carbonate buffer (CB) 60 mM, pH 10.7 Qsf (g) | 100 | 100 |

The alcohol content is adapted to solubilise the lipophilic ingredients.

B. Methods and Results

The operating procedures disclosed in Example 1 is followed with the two testosterone formulations described above.

| No | Formulations | (n) | Quantity of Testosterone (ng) recovered into the dermis at 24 H | % of Testosterone recovered into the dermis at 24 H | Statistical Mann-Whitney test * |
|---|---|---|---|---|---|
| 1 | T 0.24% + MA 2% + PG 5% + isopropanol 56% + CB | 9 | 334 ± 172 | 1.59 ± 0.82 | P value Form. 1/ Form. 2 = 0.001 |
| 2 | T 0.24% + MA 2% + IPM 2% + PG 5% + isopropanol 56% + CB | 8 | 885 ± 287 | 4.31 ± 1.40 | |

* performed on the % of Testosterone recovered in the dermis at 24 h data

These results show that at the testosterone concentration tested, the addition of isopropyl myristate induces a significant increase (at least 2.5-fold) in the dermal retention after 24 hours ($p<0.01$).

Example 4: In Vitro Absorption of Dihydrotestosterone into the Dermis

A. Chemicals and Formulations

Tritiated dihydrotestosterone [3H], is used in the preparation of pharmaceutical compositions as below.

| Formulation | 1 | 2 |
|---|---|---|
| dihydrotestosterone (DHT) (g) | 0.7 | 0.7 |
| Ethanol 95% (g) | 71 | 71 |
| isopropyl myristate (IPM) (g) | 0.5 | 1 |
| CARBOPOL ® 980 (g) | 0.5 | 0.5 |
| triethanolamine (TEA) (g) | 0.5 | 0.5 |
| water Qsf (g) | 100 | 100 |

B. Methods and Results

The operating procedures disclosed in Example 1 is followed with the two DHT formulations described above.

| No | Formulations | (n) | Quantity of DHT (ng) recovered into the dermis at 24 H | % of DHT recovered into the dermis at 24 H | Statistical Mann-Whitney test * |
|---|---|---|---|---|---|
| 1 | DHT gel with 0.5% IPM | 7 | 676 ± 186 | 2.50 ± 0.69 | P value Form. 1/ Form. 2 < 0.05 |
| 2 | DHT gel With 1.0% IPM | 6 | 1758 ± 509 | 6.67 ± .1.93 | |

* performed on the % of DHT recovered in the dermis at 24 h data

These results show that an increase of the percentage of IPM in the gel induces a significant ($p<0.05$) dermal retention of Dihydrotestosterone (at least 2-fold) after 24 hours.

Example 5: Evaluation of the Percutaneous Absorption of Progesterone Using Franz Human Skin Finite Dose Model A. Introduction The in vitro Franz human skin finite dose model has proven to be a valuable tool for the study of percutaneous absorption and the determination of the pharmacokinetics of topically applied drugs. The model uses human ex vivo cadaver or surgical skin mounted in specially designed diffusion chambers allowing the skin to be maintained at a temperature and humidity that match typical in vivo conditions (Franz, T J, "Percutaneous absorption: on the relevance of in vitro data", J Invest Derm 1975, 64:190-195.). A finite dose (for example, 4-7 mg/cm2) of formulation is applied to the outer surface of the skin and drug absorption is measured by monitoring its rate of appearance in the reservoir solution bathing the inner surface of the skin. Data defining total absorption, rate of absorption, as well as skin content can be accurately determined in this model. The method has historic precedent for accurately predicting in vivo percutaneous absorption kinetics (Franz T J, "The finite dose technique as a valid in vitro model for the study of percutaneous absorption in man." In: Skin: Drug Application and Evaluation of Environmental Hazards, Current Problems in Dermatology, vol. 7, G. Simon, Z. Paster, M. Klingberg, M. Kaye (Eds), Basel, Switzerland, S. Karger, 1978, pp 58-68).

C. Study Design

The percutaneous absorption pharmacokinetics of progesterone from two test and one reference formulations was studied using the in vitro finite dose model on human skin using a single center, open label, within donor, study of three (3) topical gel formulations containing progesterone. Each formulation was tested in triplicate on three different skin donors using the in vitro Franz finite dose skin model.

D. Study Products and Dosing

Reference Product: Commercial Progestogel (1% progesterone hydroalcholic gel) (Besins Healthcare).

Test Product(s):

New formulation #1:

| | |
|---|---|
| Progesterone | 1% |
| Ethanol (USP 190 Proof) | 72% |
| Propylene Glycol | 5% |
| Oleic acid | 2% |
| Ethyl oleate | 2% |
| PEMULEN ® TR-1 | 2% |
| Carbonate buffer (pH 10.8) | qsf 100% |

New formulation #2:

| | |
|---|---|
| Progesterone | 3% |
| Ethanol (USP 190 Proof) | 72% |
| Propylene Glycol | 5% |
| Oleic acid | 2% |
| Ethyl oleate | 2% |
| PEMULEN ® TR-1 | 2% |
| Carbonate buffer (pH 10.8) | qsf 100% |

(Carbonate buffer was prepared from 16.91 parts water, 0.070 parts sodium carbonate and 0.007 parts sodium bicarbonate.)

Dosing

5 µL formulation/cm2/skin section (dosed by pipette and rubbed in using a glass rod). The glass rod is retained for analysis as part of the mass balance accountability and for correction of the applied dose.

E. Study Procedures

1. Reagents and Source of Standards

All reagents used in this study are of analytical reagent grade or better.

2. Reservoir Medium

For the skin integrity test, the medium base consists of phosphate buffered saline (pH 7.4±0.1). For all further study conduct, the medium base consists of 0.1× PBS with 0.1% VOLPO® (a non-ionic surfactant: VOLPO® (Oleth-20) is a non-ionic surfactant known to increase the aqueous solubility of poorly water soluble compounds. VOLPO® in the reservoir solution will ensure diffusion sink conditions during percutaneous absorption, and is known not to affect the barrier properties of the test skin).

3. Diffusion Cell and Skin Preparation

Human, ex vivo trunk skin without obvious signs of skin disease is used in this study. It has been dermatomed, cryopreserved, sealed in a water-impermeable plastic bag, and stored at ~−70° C. until the day of the experiment. Prior to use it is thawed in 37° C. water, then rinsed in tap water to remove any adherent blood or other material from the surface.

Skin from a single donor is cut into multiple smaller sections large enough to fit on nominal 1.0 cm2 Franz diffusion cells. The dermal chamber is filled to capacity with a reservoir solution of phosphate-buffered isotonic saline (PBS), pH 7.4±0.1, and the epidermal chamber is left open to ambient laboratory environment. The cells are then placed in a diffusion apparatus in which the dermal reservoir solution is stirred magnetically at ~600 RPM and its temperature maintained to achieve a skin surface temperature of 32.0±1.0° C.

To assure the integrity of each skin section, its permeability to tritiated water is determined before application of the test products (Franz T J, Lehman P A: The use of water permeability as a means of validation for skin integrity in in vitro percutaneous absorption studies. Abst. J Invest Dermatol 1990, 94:525). Following a brief (0.5-1 hour) equilibrium period, $^{3}H_{2}O$ (NEN, Boston, Mass., sp. Act. ~0.5 µCi/mL) is layered across the top of the skin by dropper so that the entire exposed surface is covered (approximately 200-500 µL). After 5 minutes, the $^{3}H_{2}O$ aqueous layer is removed. At 30 minutes, the reservoir solution is collected and analyzed for radioactive content by liquid scintillation counting. Skin specimens in which absorption of $^{3}H_{2}O$ is less than 1.56 µL-equ/cm$^2$ are considered acceptable.

4. Dose Administration and Sample Collection

Prior to administration of the topical test formulations to the skin sections, a pre-dose sample is collected and the reservoir solution is replaced with a fresh solution of 0.1× PBS with 0.1% VOLPO®.

Subsequently, each test product is applied to triplicate sections of skin from the same donor. Dosing is performed using a positive displacement pipette set to deliver 5 µL formulation/cm$^2$ with the applied dose rubbed on to the skin using a glass rod. The glass rod is retained for analysis as part of mass balance accountability.

At pre-selected times after dosing (4, 8, 12, 24, 32, and 48 hours), the reservoir solution is removed in its entirety, replaced with fresh reservoir solution, and a predetermined volume aliquot saved for subsequent analysis.

After the last sample is collected, the surface is washed twice with 50:50 Methanol:Water (0.5 mL volume each time) to collect un-absorbed formulation from the surface of the skin. Following the wash, the intact skin is then removed from the chamber and extracted in 50:50 Methanol:Water.

5. Analytical Laboratory

Quantification of Progesterone is performed by High Performance Liquid Chromatography (HPLC). Briefly, HPLC is conducted on a Hewlett-Packard 1100 Series HPLC system with a diode array UV detector and, if needed, a Mass Spectroscopy (MS) using the current laboratory method. Peak areas are quantified to concentration using an external standard curve prepared daily from the neat standard.

Samples not assayed on the day of collection are stored at or below −20° C.

F. Analyses And Reports

1. Study Parameters

The following parameters are calculated:
- a) Total absorption (sum of all reservoir solutions sampled from a chamber)
- b) Rate and Extent of penetration across the study period.
- c) Surface wash and skin content.

2. Data Evaluation
- a) If any sample is <LLD (Lower Limit of Detection) then that sample may be treated as a non-data value. At the discretion of the investigator, all values <LLQ (Lower Limit of Quantification) may be declared as zero values or actual value measured for the purpose of calculating key parameters.
- b) A suspected outlier is confirmed using the Dean and Dixon Outlier test. At the discretion of the investigator, values declared as outliers may be removed from the overall summation of the data (but will be noted as such in the text or data tables).
- c) Within a chamber, if a given time-point value has been declared a non-data value, or is missing due to other reasons; the time-point value can be replaced with an interpolated value to calculate the relevant parameters. The interpolated value will be calculated on a line that connects the adjacent values as follows:
  Given 3 points: (T1,A), (T2,B) and (T3,C) with (B) missing,
  Where T=Time and A–C=measured data values
  Estimated $B=A-[((A-C)/|T1-T3|)\times(|T1-T2|)]$ 3. Statistical Evaluation Replicates within donors are averaged and standard deviation are calculated for each key parameter. Within donor averages are then collated and the across donor population mean with standard error is calculated. Differences between test articles are evaluated using the Student's t-test.

G. Results
Results are in µg/cm²

| Source | New Form. #1 1% Progesterone | New Form. #2 3% Progesterone | Progestogel Lot # 427 |
|---|---|---|---|
| Reservoir | 11.00 ± 1.74 | 6.76 ± 0.68 | 2.67 ± 0.93 |
| Skin | 3.91 ± 1.06 | 31.76 ± 12.30 | 1.07 ± 0.23 |
| Surface | 18.76 ± 0.86 | 80.01 ± 11.98 | 40.00 ± 1.32 |
| Total Recovery (%) | 93.97 ± 0.75 | 99.33 ± 0.77 | 101.40 ± 0.914 |

The formulation at 1% progesterone achieves an over 4-times greater delivery of active principle into the reservoir compartment as does the commercial Progestogel formulation with the same concentration of active (1% progesterone).

The formulation at 3% progesterone delivers less active in the reservoir than the 1% formulation over a 48 hour period, but loads a much higher amount of drug into the skin (31.7 vs 3.9 µg), thereby predicting a release of active from the skin into the reservoir over a longer time period.

FIG. 1 illustrates the penetration profiles for the three formulations tested.

Example 6: Evaluation of the Percutaneous Absorption of Estradiol Using Franz Human Skin Finite Dose Model The same protocol as that described in Example 5 is followed, with differences noted below.

Four different gel formulations containing 0.36% estradiol were tested, each with 2% oleic acid, 2% ethyl oleate, and 5% propylene glycol. The formulation variables (e.g., buffer and gelling agent) are given in Table 6-1. The cumulative drug penetration after 48 hours ranged from 1.03 to 1.77 µg, with maximal delivery occurring between 8 to 20 hours (see Table 6-3). The results are compared in Table 6-3 below with results for two lots of 0.06% estradiol gel (one lot prepared for these experiments and one sample of the commercial product, see Table 6-2 for composition of the 0.06% estradiol gel formulation), where the cumulative penetration of drug after 48 hours was about 0.07 µg, with maximal delivery occurring after eight hours. Thus, the six-fold increase in estradiol concentration (from 0.06% to 0.36%) resulted in between 15 and 25-fold increase in cumulative drug delivery. From this it can be concluded that the increased penetration cannot be based solely on increased concentration, but must also have been influenced by the formulation design.

TABLE 6-1

0.36% Estradiol Formulations

| Formulation | Composition |
|---|---|
| A | 0.36% Estradiol gel containing 2% oleic acid, 2% ethyl oleate, 5% propylene glycol Carbonate Buffer - 1.7% KLUCEL ® HF (Lot# 818-0909A01) |
| B | 0.36% Estradiol gel containing 2% oleic acid, 2% ethyl oleate, 5% propylene glycol No buffer - 3.0% CARBOPOL ® 981 (Lot# 818-0924A02) |
| C | 0.36% Estradiol gel containing 2% oleic acid, 2% ethyl oleate, 5% propylene glycol Carbonate Buffer - 2.0% PEMULEN ® TR-1 (Lot# 818-911A06) |
| D | 0.36% Estradiol gel containing 2% oleic acid, 2% ethyl oleate, 5% propylene glycol Carbonate Buffer - 3.0% KLUCEL ® HF (Lot# 818-0911A02) |

TABLE 6-2

Estrogel ® composition

| Formulation | Estrogel ® |
|---|---|
| Estradiol | 0.06% |
| Ethanol | 40% |
| CARBOPOL 980 ® | 1% |
| triethanolamine (TEA) | 1% |
| water Qsf | 100% |

TABLE 6-3

Total Absorption Across Skin Donors
Percutaneous Absorption of Estradiol through Intact Human Cadaver Skin over 48 hours from a Single Application. Mean ± SE as Percent of Applied Dose and Total Mass (µg/cm²).

| Parameter | Formulation A | Formulation B | Formulation C | Formulation D | Estrogel ® (Lot# 769-0929A02) | Estrogel ® (Commercial product) |
|---|---|---|---|---|---|---|
| 24 hr Cumulative Penetration (µg/cm²) | 0.835 ± 0.007 | 0.725 ± 0.404 | 0.993 ± 0.608 | 0.521 ± 0.181 | 0.031 ± 0.026 | 0.024 ± 0.021 |
| 48 hr Cumulative Penetration (µg/cm²) | 1.556 ± 0.239 | 1.570 ± 0.674 | 1.765 ± 0.862 | 1.031 ± 0.421 | 0.071 ± 0.011 | 0.065 ± 0.008 |
| 48 hr Cumulative Penetration (%) | 8.643 ± 1.328 | 8.721 ± 3.746 | 9.805 ± 4.787 | 5.728 ± 2.340 | 2.358 ± 0.369 | 2.166 ± 0.255 |

These results show that Formulation C gave maximal delivery, about 25-fold greater than the ESTROGEL® formulation. Formulation C was subsequently studied at lower estradiol concentrations to determine a dose-response. The results (FIG. 2) show that the amount of drug delivered increased with increasing concentration of estradiol applied. The results obtained at the highest concentration (0.36%) agree well with the data obtained in this example (Table 6-3, Formulation C). In addition, the values obtained for ESTROGEL® (0.06% estradiol) are in close agreement between the two studies, further supporting their reliability.

Figure 2:
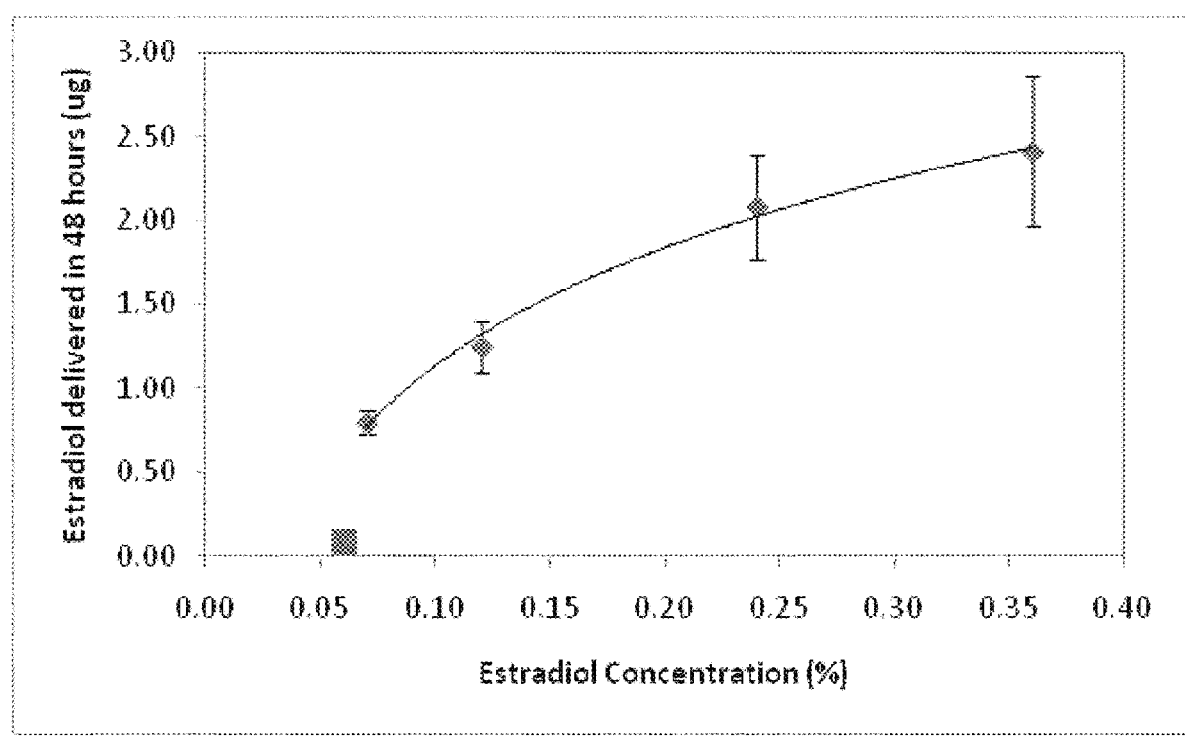
FIG. 2 represents the amount of estradiol delivered (µg) through the skin in 48 hours relative to the drug loading in one exemplary formulation (diamonds) and in comparison to ESTROGEL® (0.06% estradiol gel, square) (Ascend Therapeutics).

The results depicted in FIG. 2 also show that even at roughly equivalent estradiol concentrations (0.07% vs. 0.06%), the new formulation (C) delivered about 10-fold more drug than the ESTROGEL® formulation. Thus, the compositions described herein make it possible to deliver an equivalent dose to the existing commercial transdermal gel product with 10 times less applied volume, such as with Formulation C containing estradiol at 0.07%. This represents a significant advantage, including safety advantages, regulatory advantages and cost savings due to the need for so much less product to provide an equivalent dose. For example, regulatory agencies often encourage the development of products that contain a minimal amount of active agent required for therapeutic efficacy.

Example 7: Evaluation of Formulation Influences on Percutaneous Absorption of Estradiol Using Franz Human Skin Finite Dose Model In order to study the influence of the penetration enhancers and of the co-solvent on the percutaneous absorption of the active in the new gel formulations, a 2-phase, statistically designed, experiment was conducted.

In the first phase, the influence of varying oleic acid and co-solvent (propylene glycol) concentrations, together with the estradiol concentration, on the total amount of active delivered was studied.

In the second phase, the influence of varying the ethyl oleate and the estradiol concentrations on the amount of active delivered and on the time profile of the delivery was studied.

The "Design-Expert" statistical software (available from StatEase at www.statease.com) was used to generate the experimental data points used in the study.

The same protocol as that described in Example 5 is followed, with differences noted below.

A. First Phase of the Study

For the first phase, a combined D-optimal design with oleic acid and propylene glycol as mixture components and with estradiol as numeric factor (process) is used. The oleic acid and propylene glycol concentrations are varied in such a way that the total of their two concentrations remained constant and equal to 7%, thus minimizing potential differences in solubility between formulations.

The Table below summarizes the formulations that are prepared and tested in triplicate on samples from two different donors. Each formulation contained in addition: ethanol at 72%, ethyl oleate at 2% and PEMULEN® TR-1 at 2%.

| Formulation # | Run | Estradiol % | Oleic Acid % | Propylene Glycol % | Carb. Buffer % |
|---|---|---|---|---|---|
| 206 | 6 | 0.05 | 0.00 | 7.00 | 16.95 |
| 213 | 13 |  | 0.00 | 7.00 | 16.95 |
| 214 | 14 |  | 3.47 | 3.53 | 16.95 |
| 208 | 8 |  | 7.00 | 0.00 | 16.95 |
| 216 | 16 |  | 7.00 | 0.00 | 16.95 |
| 211 | 11 | 0.16 | 1.40 | 5.60 | 16.84 |
| 215 | 15 |  | 4.90 | 2.10 | 16.84 |
| 205 | 5 | 0.26 | 7.00 | 0.00 | 16.74 |
| 210 | 10 |  | 7.00 | 0.00 | 16.74 |
| 207 | 7 | 0.28 | 0.00 | 7.00 | 16.72 |
| 201 | 1 |  | 3.35 | 3.65 | 16.72 |
| 212 | 12 |  | 3.50 | 3.50 | 16.73 |
| 219 | 19 | 0.38 | 5.60 | 1.40 | 16.62 |
| 204 | 4 | 0.41 | 1.46 | 5.54 | 16.59 |
| 218 | 18 |  | 3.50 | 3.50 | 16.59 |
| 203 | 3 | 0.50 | 0.00 | 7.00 | 16.50 |
| 220 | 20 |  | 0.00 | 7.00 | 16.50 |
| 217 | 17 |  | 3.21 | 3.79 | 16.50 |
| 202 | 2 |  | 7.00 | 0.00 | 16.50 |
| 209 | 9 |  | 7.00 | 0.00 | 16.50 |

Additionally, the following steps are performed:

Potency Assessment

The Estradiol potency of the final formulations can be determined in triplicate by HPLC/UV. Potency can be calculated as (w/v) to calculate the mass amount of Estradiol in the applied dose, so that the percentage absorbed of the applied dose can be calculated. Potency also can be calculated, correcting for density, as (w/w), to compare with the target potency of the prepared formulations indicated in the table above. Estradiol Potency must be within ±5.0% to be acceptable for this study. In the data analysis the actual estradiol concentrations of each formulations are used.

Formulation preparation:

1. Add ethanol and propylene glycol and mix until uniform.
2. Slowly add estradiol and mix until completely dissolved.
3. Add oleic acid and mix until uniform.
4. Add ethyl oleate and mix until uniform.
5. Slowly add PEMULEN® TR-1 and mix well until completely hydrated.
6. Slowly add the carbonate buffer solution to the above gel matrix and mix until uniform.

B. Second Phase of the Study

For the second phase, a Response-surface design with a Central Composite Structure is used.

The formulations to be studied are shown in the following table, with the addition of: ethanol at 72%, PEMULEN® TR-1 at 2%, oleic acid at 2%, and propylene glycol at 5%.

| Formulation # | Run | A: Estradiol % | B: EthylOleate % | Carb. Buffer % |
|---|---|---|---|---|
| 305 | 5 | 0.05 | 1.00 | 17.95 |
| 311 | 11 | 0.12 | 0.29 | 18.59 |
| 302 | 2 |  | 1.71 | 17.18 |
| 303 | 3 | 0.28 | 0.00 | 18.73 |
| 304 | 4 |  | 1.00 | 17.73 |
| 307 | 7 |  |  | 17.73 |
| 308 | 8 |  |  | 17.73 |
| 310 | 10 |  | 2.00 | 16.73 |
| 301 | 1 | 0.43 | 0.29 | 18.27 |
| 306 | 6 |  | 1.71 | 16.86 |
| 309 | 9 | 0.50 | 1.00 | 17.50 |

The rest of the experimental procedure is as that of the first phase of the study.

C. Results from the First Phase of the Study

As described in Section A, above under the paragraph "Potency Assessment," each formulation is checked for its actual estradiol concentration. The measured values are shown in the Table below, and are used in the data analysis.

| F # | Target Conc (%) | Measured Conc (%) |
|---|---|---|
| 201 | 0.28 | 0.29 |
| 202 | 0.50 | 0.48 |
| 203 | 0.50 | 0.48 |
| 204 | 0.41 | 0.43 |
| 205 | 0.26 | 0.24 |
| 206 | 0.05 | 0.05 |
| 207 | 0.28 | 0.27 |
| 208 | 0.05 | 0.05 |
| 209 | 0.50 | 0.49 |
| 210 | 0.26 | 0.24 |
| 211 | 0.16 | 0.16 |
| 212 | 0.28 | 0.28 |
| 213 | 0.05 | 0.05 |
| 214 | 0.05 | 0.06 |
| 215 | 0.16 | 0.16 |
| 216 | 0.05 | 0.04 |
| 217 | 0.50 | 0.50 |
| 218 | 0.41 | 0.42 |
| 219 | 0.38 | 0.37 |
| 220 | 0.50 | 0.42 |

The total penetration data (amount of active having penetrated in the reservoir compartment after 48 hours) was of sufficient quality to allow analysis in a statistically significant manner with quadratic models for the mixture and process parts of the design.

Figure 3:
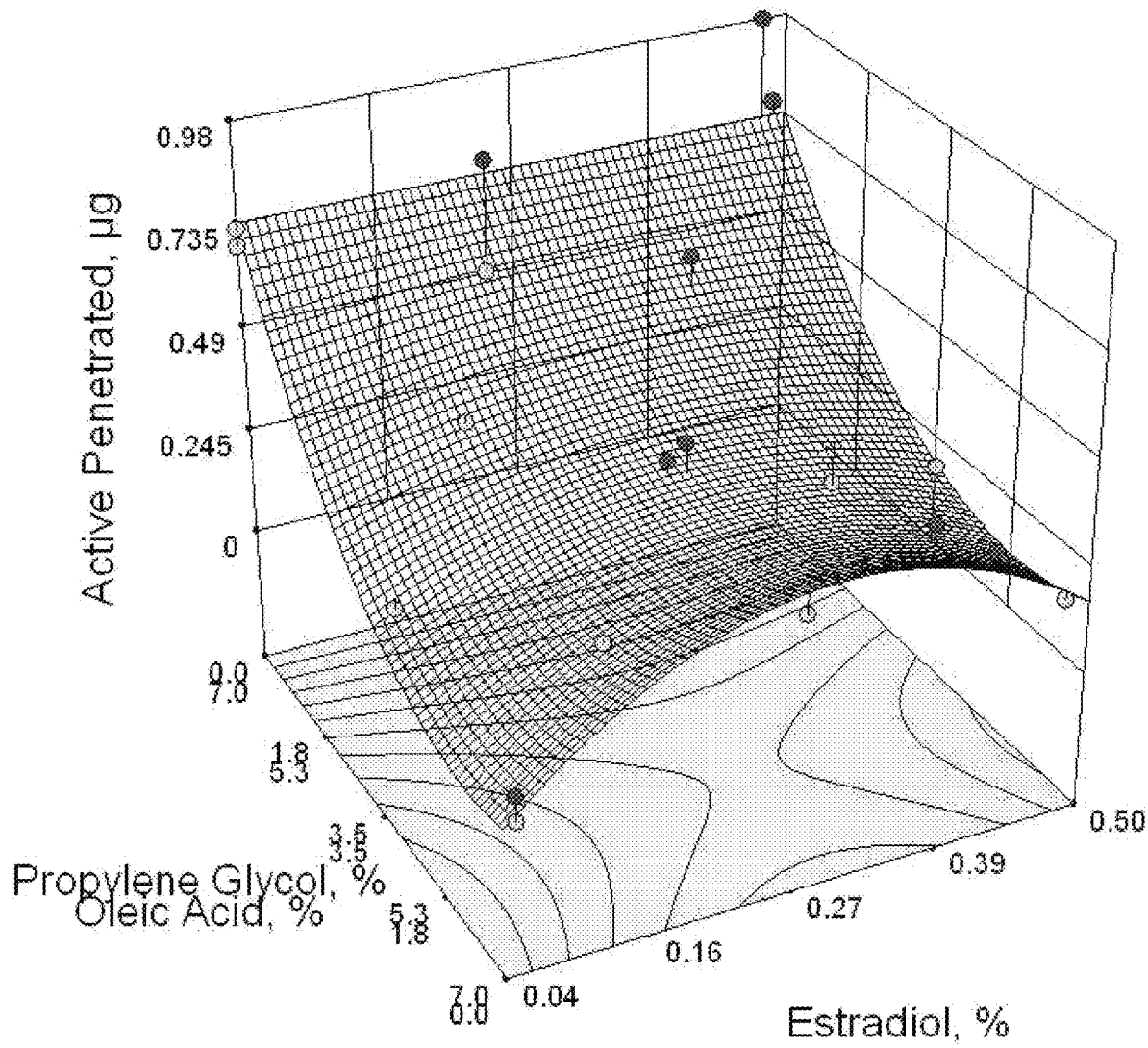
FIG. 3 represents the effect of the oleic acid, propylene glycol and estradiol concentrations on the total penetration of estradiol (g) over 48 hours.

FIG. 3 illustrates the response surface obtained. As propylene glycol (front of the graph) is gradually replaced by oleic acid (back of the graph), the variation of absorption as a function of the estradiol concentration goes from a bell-shaped curve to a flat, constant curve.

A bell-shaped curve results from a strong dependency of the absorption on the concentration of therapeutically active agent in the formulation, as is the case, for example, for formulations having high propylene glycol and low oleic acid concentrations.

This dependency on the concentration of therapeutically active agent is not desirable, since compositions able to achieve efficient delivery over greater ranges of active agent concentrations are generally preferable from a regulatory and commercial perspective.

At the other end of the oleic acid/propylene glycol axis, i.e. in the high oleic acid/low propylene glycol region, the dependency of the absorption on the estradiol concentration is not observed, and the total absorption reaches higher absolute levels, most likely due to the efficiency of the fatty acid as penetration enhancer. The reproducibility of the experimental data points is not good, however, as can be seen in FIG. 3 for the replicates conducted at 0.26 and 0.5% estradiol. This lack of reproducibility is confirmed by looking at the standard error graph for the same dataset (not shown—error increases with increasing oleic acid concentrations), and also at the individual data for each experimental point, which consisted of 3 replicates on two different donors. Such a spread in absorption from one donor sample to the other, and even between replicates on the same donor sample indicates instability in the system. Indeed, some experiments deliver large amounts of active while other experiments, despite all experimental parameters being kept constant, deliver significantly less active. Such behaviour is not desirable in a pharmaceutical composition, because when translated into the clinic, these formulations could give large patient-to-patient variations or even within-patient variations from application-to-application. For these reasons, it may be advantageous to select ranges of fatty acid and co-solvent concentrations that do not encompass the highest and lowest propylene glycol/oleic acid concentrations studied here.

Figure 4:
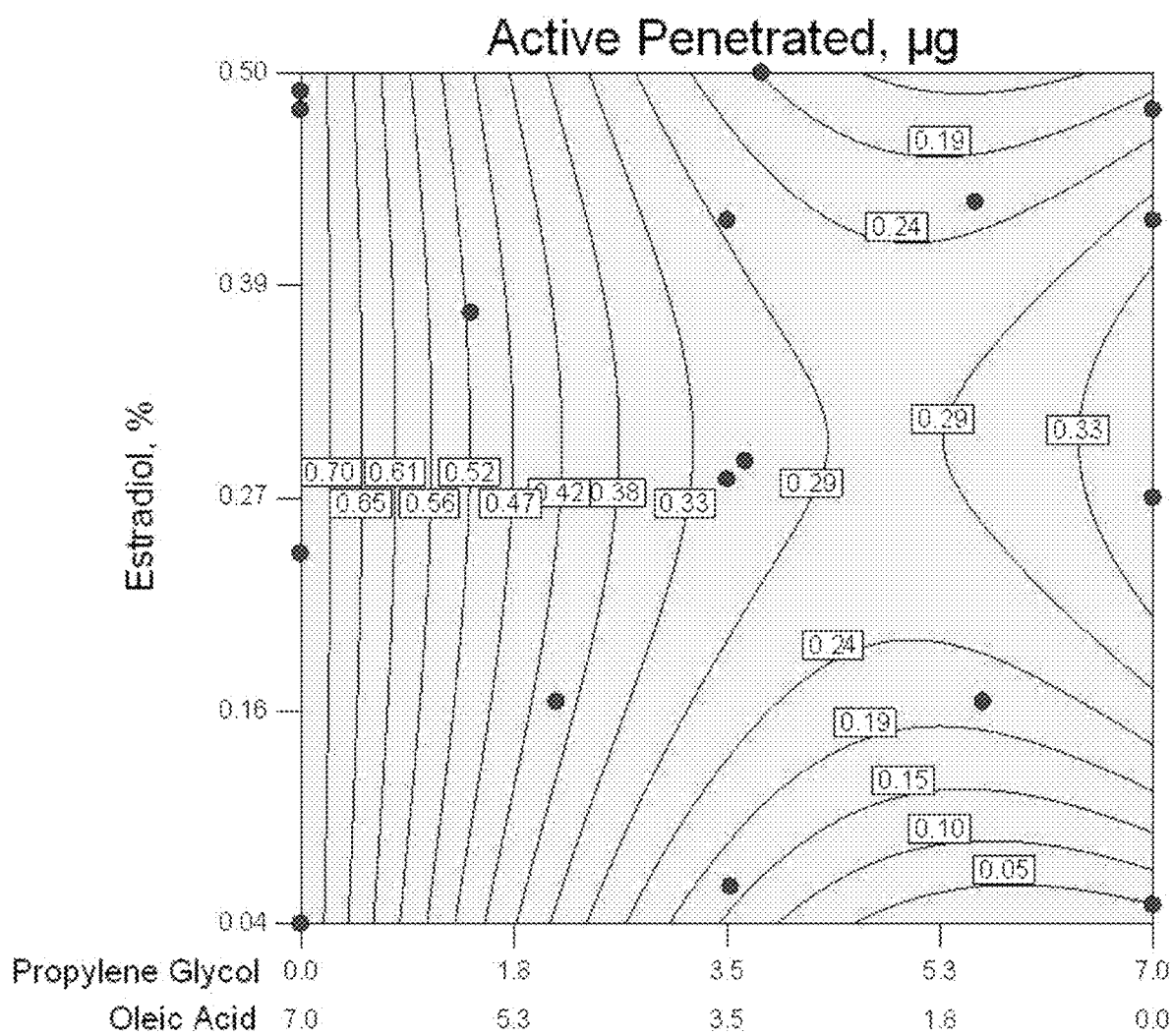
FIG. 4 represents the effect of the oleic acid, propylene glycol and estradiol concentrations on the total penetration of estradiol (g) over 48 hours.

Further illustrating this point, FIG. 4 represents a top-down view of the data illustrated three-dimensionally in FIG. 3. The middle region, centered around 2% oleic acid and 5% propylene glycol, appears to be the most desirable for a composition that exhibits absorption with minimal dependency on active agent concentration (the problem seen with higher concentrations of propylene glycol) while achieving strong reproducibility between data points (contrary to the data obtained with higher concentrations of oleic acid), even though not providing the highest delivery of active.

In specific embodiments, therefore, the fatty acid permeation enhancer is present in an amount of from 0.01% to 5%, including from 0.05% to 3.5%, such as 1% to 3%, by weight based on the total weight of the composition.

Additionally, in specific embodiments, the co-solvent (such as propylene glycol) is present in an amount of from 0.01% to 7%, including from 3% to 7%, such as from 4% to 6%, by weight based on the total weight of the composition.

D. Results from the Second Phase of the Study

Figure 5:
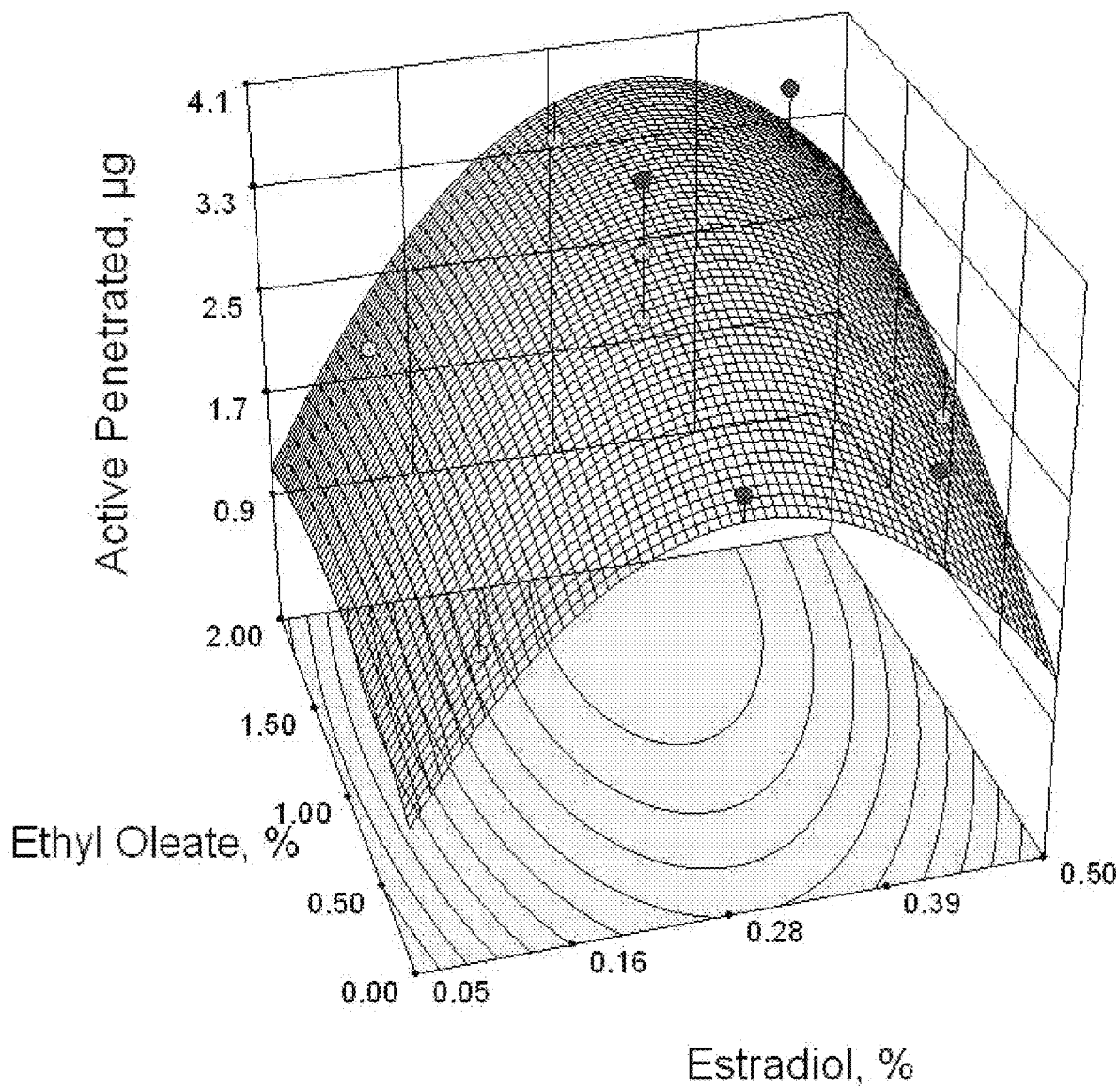
FIG. 5 represents the effect of the ethyl oleate and estradiol concentrations on the total penetration of estradiol (µg) over 48 hours.
Figure 6:
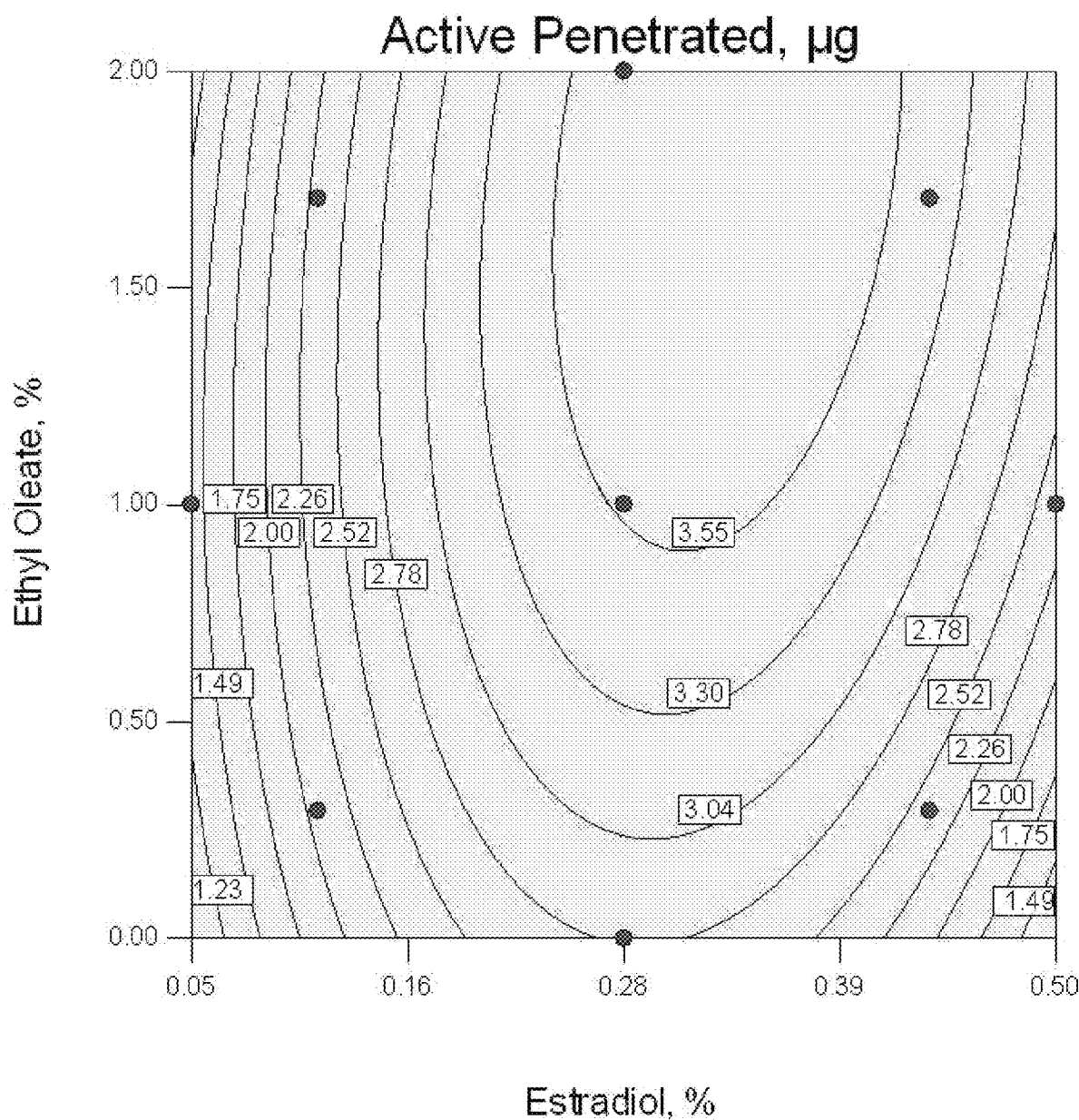
FIG. 6 represents the effect of the ethyl oleate and estradiol concentrations on the total penetration of estradiol (kg) over 48 hours.

FIGS. 5 and 6 illustrate the influence of ethyl oleate and estradiol concentration on the total absorption over 48 hours. The variation of estradiol concentration affects the absorption in a bell-shaped fashion, as already illustrated in the first phase of the study at the corresponding oleic acid and propylene glycol concentrations. The addition of ethyl oleate has the effect of increasing the total amount of absorption and also of shifting the optimal estradiol concentration (i.e. the estradiol concentration corresponding to maximum absorption) to higher values. This phenomenon is most clearly visible in FIG. 6.

The main effect of the ester (ethyl oleate), however, as already described in examples 1 to 4, is to modify the delivery profile over time, providing a sustained release effect. To illustrate this phenomenon, the graphs representing time courses of the absorption fluxes for the 11 compositions tested have been grouped in 3 categories, illustrated in FIGS. 7 to 9.

Figure 7:
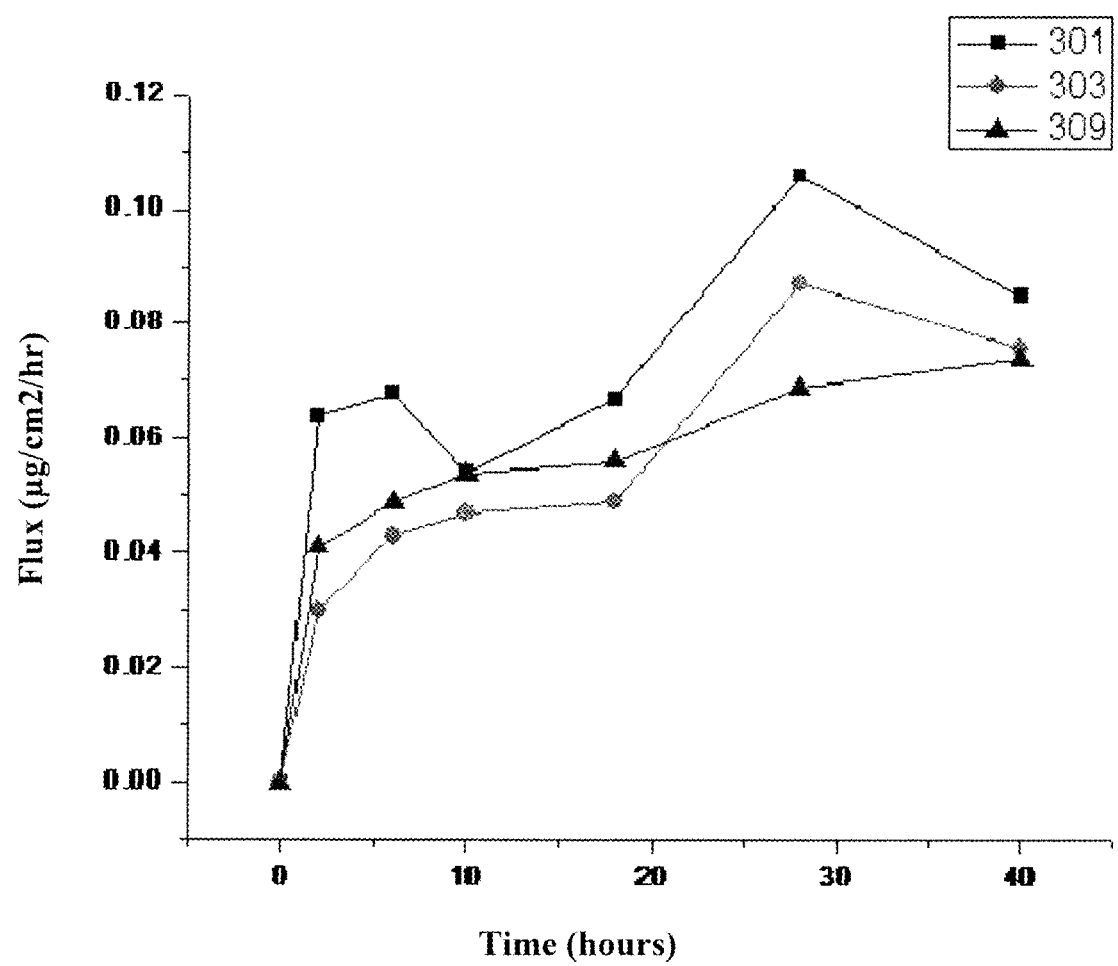
FIG. 7 represents the flux profile (g/cm2/hr) over time for three compositions tested in Example 7. (■-Formulation 301; ●-Formulation 303; ▲-Formulation 309.)

FIG. 7 shows flux profiles for a first group which trigger after about 20 hours an increase in flux, leading to a profile where the dose escalates with time. This is not desirable for a product where a strong delivery within hours of application is sought followed by a plateau of steady release of the drug. The three data points illustrated in FIG. 7 all belong to the "low ethyl oleate"-"high estradiol" corner in the graph from FIG. 6.

Figure 8:
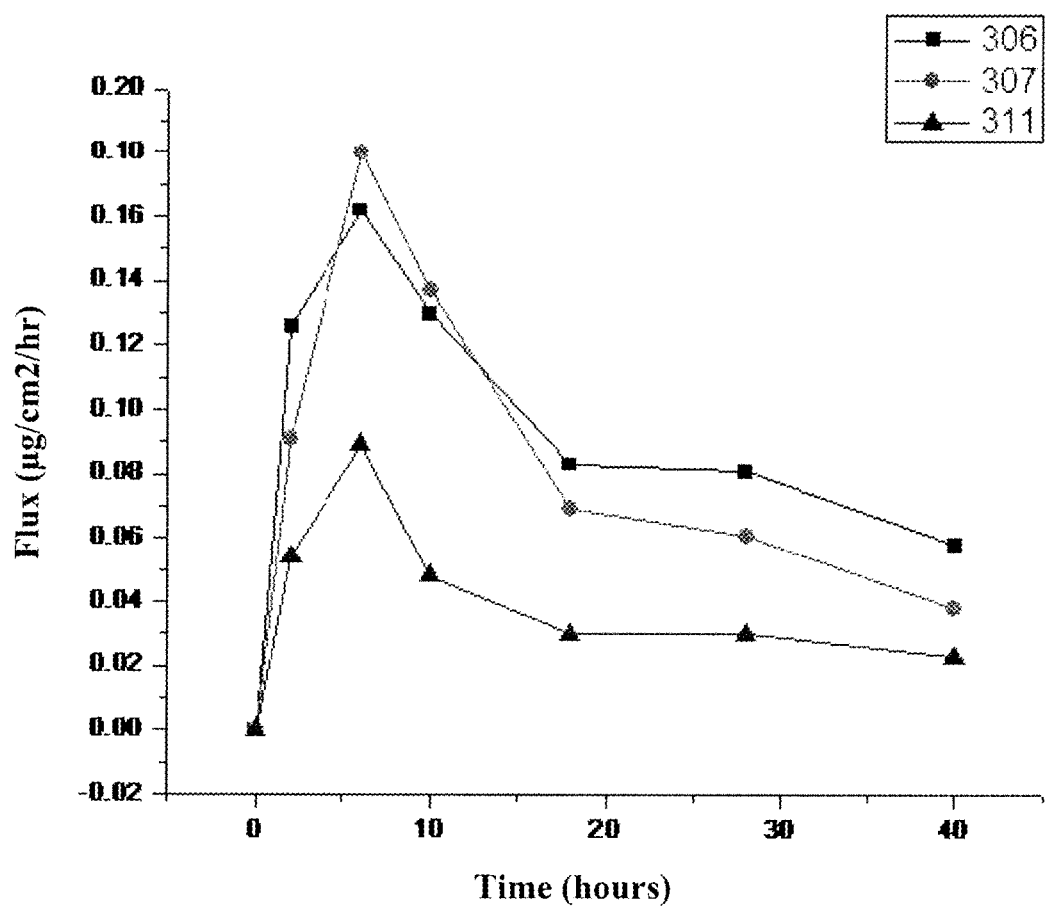
FIG. 8 represents the flux profile (g/cm2/hr) over time for three compositions tested in Example 7. (■-Formulation 306; ●-Formulation 307; ▲-Formulation 311.)

FIG. 8 displays flux profiles of a second group, where the flux decreases rapidly after the peak occurring at 6 hours post administration. This profile is typical of a number of prior art compositions, which achieve fast and efficient delivery within the first few hours post administration, but which lack steady release over a longer term, i.e. 24 or even 48 hours. The three data points illustrated in FIG. 8 are along the Y=X line in the graph from FIG. 6.

Figure 9:
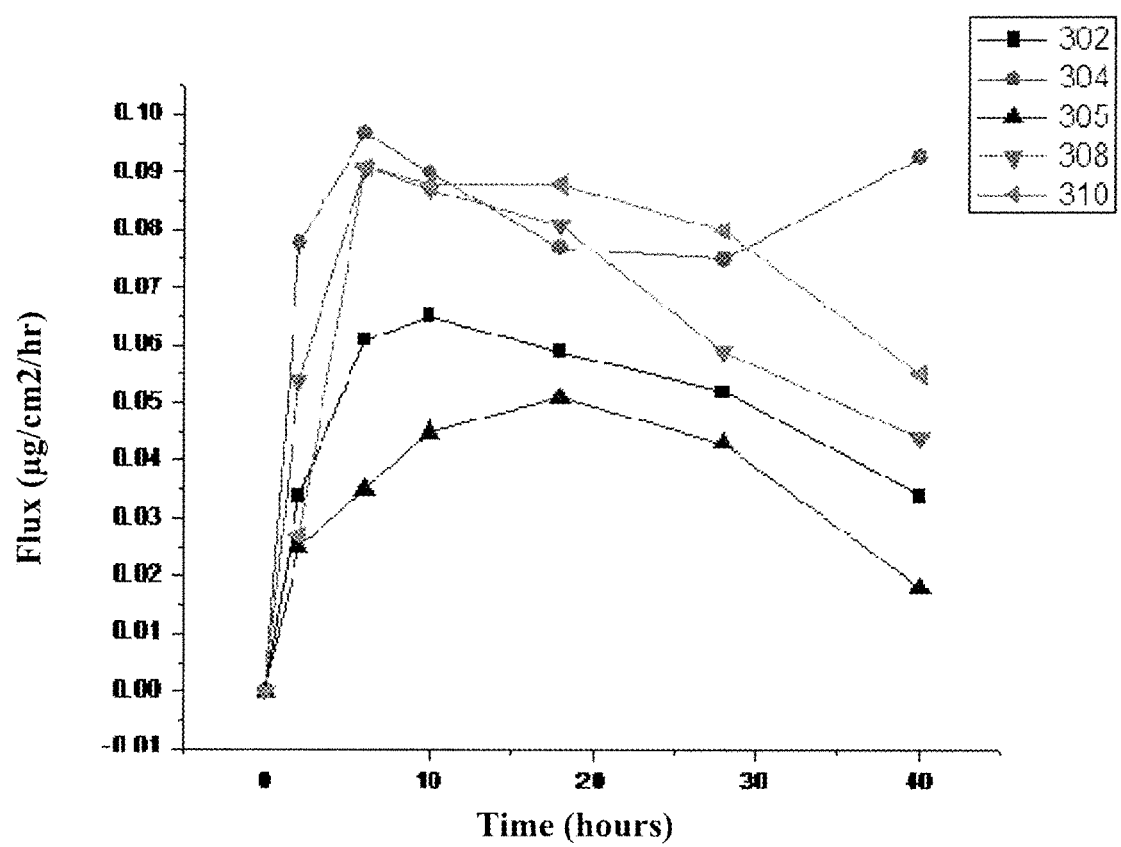
FIG. 9 represents the flux profile (g/cm2/hr) over time for five compositions tested in Example 7. (■-Formulation 302; ●-Formulation 304; ▲-Formulation 305; ▼-Formulation 308; ◄-Formulation 310.)

Finally, FIG. 9 displays profiles of experimental data points with an early, rapid rise in flux, followed by a steady flux level over 2 days, i.e., a sustained release, storage depot effect. This type of flux is desirable in many therapies, where both rapid attainment of therapeutic blood concentrations and sustained blood concentrations of drug are desired. The compositions that achieve this type of profile are compositions in the "high ethyl oleate"-"low estradiol" half of the graph from FIG. 6 (in other words, above the Y=X line).

This qualitative analysis of the flux profiles over time demonstrates that a sustained release of active agent is achieved in a satisfactory manner when the fatty acid ester is present in a greater amount than the active agent, such as the fatty acid ester being present in an amount at least four times greater than that of the active agent, on a weight:weight basis.

Figure 10:
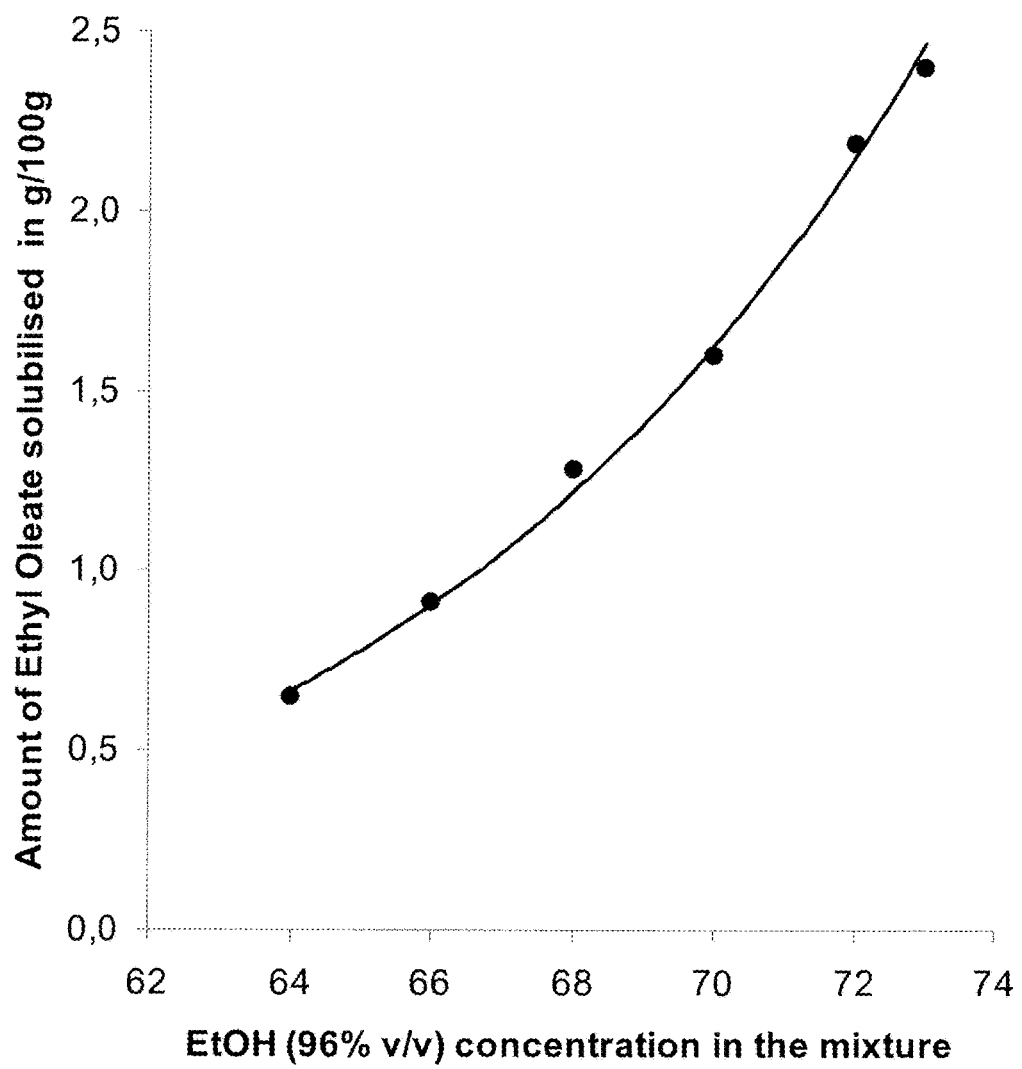
FIG. 10 represents the solubility of ethyl oleate (g/100 g) as a function of ethanol (96%) concentration (v/v) in a mixture containing 0.24% estradiol, 5% propylene glycol and 2% oleic acid, all by weight of the total weight of the composition.

In particular, it appears that the more ester is present in the composition, the better the storage depot effect is. This factor suggests that one should aim to include as much fatty acid ester in the composition as possible. An upper limit is imposed, however, by the solubility of the fatty acid ester in the composition. As an example, FIG. 10 illustrates the amount of ethyl oleate that can be dissolved, at room temperature, as a function of the ethanol (96% v/v) concentration in a formulation made up with:

0.24% estradiol;

5% propylene glycol; and

2% oleic acid

Qsf water.

From FIG. 10 and the Table below, it is apparent that in a formulation comprising 72% ethanol, a maximum of 2.2% ethyl oleate can be dissolved.

| EtOH (96% v/v) concentration in the mixture | Amount of Ethyl Oleate solubilised in g/100 g |
| --- | --- |
| 64% | 0.65 g/100 g |
| 66% | 0.91 g/100 g |
| 68% | 1.28 g/100 g |
| 70% | 1.60 g/100 g |
| 72% | 2.19 g/100 g |
| 73% | 2.40 g/100 g |

Example 8: Skin Sensitization Studies

Previous studies have reported skin irritation problems with transdermal compositions comprising high amounts of co-solvents, such as propylene glycol, at the amounts used in some embodiments described herein, such as at about 5% (w/w). To determine whether the compositions described herein are irritating, and thus possibly not suitable for widespread clinical use, skin sensitization studies are conducted in guinea pigs and rabbits, using the following formulations:

K36 Active:

| Chemical Name | % w/w |
| --- | --- |
| Purified water USP | 16.91 |
| Alcohol USP 190 Proof | 71.95 |
| Propylene Glycol USP/EP | 5.00 |
| Super Refined Oleic Acid NF | 2.00 |
| Ethyl Oleate NF | 2.00 |
| Estradiol USP | 0.36 |
| Hydroxypropyl cellulose NF (KLUCEL ® HF) | 1.70 |

-continued

| Chemical Name | % w/w |
| --- | --- |
| Sodium Bicarbonate USP | 0.007 |
| Sodium Carbonate NF | 0.07 |

P36 Active:

| Chemical Name | % w/w |
| --- | --- |
| Purified water USP | 16.91 |
| Alcohol USP 190 Proof | 71.65 |
| Propylene Glycol USP/EP | 5.00 |
| Super Refined Oleic Acid NF | 2.00 |
| Ethyl Oleate NF | 2.00 |
| Estradiol USP | 0.36 |
| PEMULEN ® TR-1 | 2.00 |
| Sodium Bicarbonate USP | 0.007 |
| Sodium Carbonate NF | 0.07 |

K36 Placebo:

| Chemical Name | % w/w |
| --- | --- |
| Purified water USP | 16.91 |
| Alcohol USP 190 Proof | 72.30 |
| Propylene Glycol USP/EP | 5.00 |
| Super Refined Oleic Acid NF | 2.00 |
| Ethyl Oleate NF | 2.00 |
| Hydroxypropyl cellulose NF (KLUCEL ® HF) | 1.70 |
| Sodium Bicarbonate USP | 0.007 |
| Sodium Carbonate NF | 0.07 |

P36 Placebo:

| Chemical Name | % w/w |
| --- | --- |
| Purified water USP | 16.91 |
| Alcohol USP 190 Proof | 72.00 |
| Propylene Glycol USP/EP | 5.00 |
| Super Refined Oleic Acid NF | 2.00 |
| Ethyl Oleate NF | 2.00 |
| PEMULEN ® TR-1 | 2.00 |
| Sodium Bicarbonate USP | 0.007 |
| Sodium Carbonate NF | 0.07 |

These studies are conducted to evaluate the potential of the test compositions, K36 Active and P36 Active, to cause or elicit skin sensitization reactions (allergic contact dermatitis) via topical patch applications in animal models.

Guinea Pigs: The compositions are applied by closed topical patch and Hilltop Chamber application to Crl:HA (Albino Hartley) Guinea Pigs. During the induction phase, three treatment groups of five animals/sex/group were administered K36 Placebo, P36 Placebo, or the positive control, Hexylcinnamic aldehyde (HCA 100%), while the remaining two treatment groups of ten animals/sex/group are administered the test compositions, K36 Active or P36 Active. During the challenge phase, each placebo group is administered the respective test composition, and the positive control receives 50% HCA in mineral oil (HCA 50%). During both phases, all groups are administered the placebos, positive control, or test compositions by dermal application at 0.4 mL/dose. During the induction phase, the placebos, positive control and test compositions are administered once a week for 3 weeks on Days 1, 8 and 15, followed by a 2 week washout period, while during the challenge phase, the positive control and test articles are administered once on Day 29.

For the duration of the study, observations for morbidity, mortality, injury, and the availability of food and water are conducted twice daily for all animals. In addition, body weights for all animals are measured and recorded prior to randomization (Day −7), prior to each test compositions administration (with the exception of Day 15, body weights were recorded approximately 6 hours postdose after unwrapping), and the day prior to termination (Day 31). During the challenge phase only, dermal irritation scoring for skin sensitization is conducted at approximately 24 and 48 hours after patch removal (post dose). At study termination, the animals are euthanized by carbon dioxide inhalation.

Dermal irritation scores recorded at 24 and 48 hours post dose during the challenge phase indicated that sensitization did not occur following the administration of induction doses and subsequent two week washout period. Irritation scores in the K36 Active and P36 Active groups were generally equivalent or lower than scores recorded for the K36 Placebo and P36 Placebo groups. Additionally, reduced body weight gain was observed in the K36 Active and P36 Active when compared with the respective placebo groups. These lower body weight gains were considered to be test article related but not adverse.

Rabbits: This study is conducted to evaluate the potential dermal irritant and/or corrosive effects of the test compositions. One treatment group of three female New Zealand White Hra:(NZW)SPF albino rabbits is administered active formulations K36 and P36, and their respective placebos, to one of the four dorsal sites at a dose level of 0.5 mL/site. The placebos and test articles are administered to the respective test sites on each animal via dermal application, once daily, for 3 consecutive days.

Observations for morbidity, mortality, injury, and the availability of food and water are conducted twice daily for all animals. Body weights are measured and recorded pre-dose. Dermal irritation scores are conducted within 30-60 minutes, and at 4 and 24 hours post dose on Days 1 and 2. On Day 3, the test sites are scored within 30-60 minutes, and at 4, 24, 48, and 72 hours post dose. Additional irritation scores are conducted on Days 8 and 15 to fully evaluate the reversibility or irreversibility of the effects observed. At study termination, all animals are euthanized, and the carcasses are discarded without further evaluation.

Minimal to mild erythema and edema was observed for both K36 and P36 Placebo and Active formulations. P36 Placebo and P36 Active appeared to cause slightly more irritation than K36 Placebo and K36 Active, though these differences were minimal. A slight decrease in body weight was observed for all three animals and was considered to be test article related, but not adverse.

These studies demonstrate that the compositions described herein, comprising about 5% propylene glycol, are not irritating, and do not give rise to significant skin sensitization effects. Thus, these factors would not limit their clinical use.

Example 9: 21-Day Dermal Toxicity Study in Rabbits

This study is conducted to evaluate the potential toxicity of the two formulations of the test compositions described above, K36 Active and P36 Active, and their respective placebos when administered once a day via dermal application for 21 consecutive days to two treatment groups of ten male and ten female New Zealand White Hra:(NZW)SPF albino rabbits.

Both the K36 Active and the P36 Active are formulated at an active concentration of 0.36% estradiol. The test articles are administered at a dose volume of approximately 0.85 to 1.11 mL. Two additional groups of ten animals/sex will serve as the control and receive the placebos, K36 Placebo and P36 Placebo.

Observations for morbidity, mortality, injury, and the availability of food and water are conducted twice daily for all animals. Clinical observations are conducted weekly. Test sites are evaluated for erythema and edema daily during the first week of dosing, and weekly thereafter. Body weights are measured and recorded weekly. Food consumption is measured and recorded daily. Blood and urine samples for clinical pathology evaluations are collected from all animals pretest and prior to the terminal necropsy. At study termination, necropsy examinations are performed and organ weights are recorded. Selected tissues are microscopically examined for animals that received P36 Active and Placebo. Tissues from the other two groups on study are held for possible future reference.

There was no test composition-related change in body weight and no clear test composition-related clinical findings. Possible test composition-related clinical findings included inappetance, aggressive behavior, and vocalization. These findings were limited to one animal per sex per group treated with either K36 Active or P36 Active, and were not observed in either placebo group.

Very slight (barely perceptible) erythema was observed sporadically throughout the study with similar or lower frequency in the K36 Active and P36 Active than in the respective placebo groups. These findings were considered to be primarily related to the vehicle and not test composition-related.

Test composition-related, but not adverse, decreases in food consumption were observed in both the K36 Active and P36 Active groups when compared with the respective placebo groups. Male food consumption was more severely affected (18.4%-19.2%) and frequently statistically significant, whereas female food consumption was moderately affected (6.5%-11.1%) and only occasionally statistically significant.

Test composition-related changes in hematology parameters included moderate decreases in erythrocytes, hemoglobin, hematocrit, reticulocytes, and platelets in both the K36 Active and P36 Active dose groups. Total leukocytes and lymphocytes were also decreased in these groups.

Test composition-related changes in clinical chemistry parameters included increased aspartate aminotransferase (AST), alanine aminotransferase (ALT), γ-glutamyltransferase (GGT), sorbitol dehydrogenase (SDH), urea nitrogen, and creatinine, and decreased triglycerides in both the K36 Active and P36 Active groups. The increases in the liver enzymes tended to be slightly greater in the males receiving P36 than in those receiving K36. The increases in urea nitrogen and creatinine were minimal and may have been secondary.

There were no test composition-related changes in coagulation or urinalysis parameters.

There were no test composition-related macroscopic findings in the males in this study. Test composition-related macroscopic observations in females in the P36 Active group included oviduct cysts in three animals and an abdominal cavity adhesion in which the uterus and cervix was adhered to the abdominal wall in one animal. A likely test composition-related macroscopic observation of red discoloration of the uterine horn and body was made in one female rabbit in the K36 Active group. Though microscopic analysis was not performed, it is likely that this observation correlated to lesions similar to those seen in the P36 Active female rabbits.

Test composition-related statistically significant alterations in organ weights occurred in the liver, spleen and thymus weights of both males and females in both the P36 Active and K36 Active groups, and in the uterus with cervix weights of the females from both the P36 Active and K36 Active groups.

Test composition-related microscopic alterations occurred within the liver, spleen and thymus of males and females, the prostate and seminal vesicles in males, and the oviducts, uterus with cervix and vagina of females.

Within the liver, there was a diffuse depletion of intrahepatocellular glycogen stores. In addition there was a minimal to mild bile duct hyperplasia. The biliary hyperplasia was possibly a direct test article effect, as estrogens have been shown to stimulate cholangiocyte proliferation (LeSage, G., S. Glaser and G. Alpini. "Regulation of Cholangiocyte Proliferation." *Liver* 21 (2001): 73-80.).

Within the spleen, there was a minimal to moderate hyperplasia of the reticuloendothelial macrophages which was occasionally accompanied by increased erythrophagocytosis, an increase in pigmented (hemosiderin-laden) macrophages and rarely by dilation of the splenic red pulp sinusoids. In addition, there was minimal to moderate depletion of the splenic lymphoid population in treated animals. These alterations may both be direct test composition effects as estrogens have been shown in rats to stimulate reticuloendothelial cells of the spleen resulting in increased phagocytosis (Steven, W. M. and T. Snook. "The Stimulatory Effects of Diethylstilbesterol and Diethylstilbesterol Diphosphate on the Reticuloendothelial Cells of the Rat Spleen." *American Journal of Anatomy* 144.3 (1975): 339-359), and also, high levels of estrogens have been shown to cause decreases in both T- and B-cell populations within the spleen of rats (Burns-Naas, L. A., B. J. Meade and A. E. Munson. "Toxic Response of the Immune System." *Cassarett & Doull's Toxicology: The Basic Science of Poisons*. Ed. Curtis D. Klaassen. New York: McGraw-Hill, 2001, 419-470.).

Thymic changes consisted of mild to severe generalized lymphoid depletion. Estrogens have been shown to cause thymic depletion (Burns-Naas, supra).

Microscopic alterations within the prostate gland and seminal vesicles of treated animals included hypertrophy of the smooth muscle associated with both of these glands, and occasional animals had increased fibroplasia with the subepithelial stroma resulting in thickening of the intraglandular septa in the prostate gland. In addition to these stromal changes, there was a dysmaturity or regression of the glandular epithelium, meaning that the epithelium was of decreased maturity (increased immaturity) compared to other features of the gland such as increased luminal diameter.

Within treated females, there was mild to severe mucification of the vaginal epithelium and mild to moderate hypertrophy of the vaginal smooth muscle. A similar finding was present in the epithelium of the cervical region of the uterus. A decidual reaction (Zook, B. C., O. A. Janne, A. A. Abraham, and H. A. Nash. "The Development and Regression of Deciduosarcomas and Other Lesions Caused by Estrogens and Progestins in Rabbits." *Toxicologic Pathology* 29.4 (2001): 411-416; Jaane, O. A., B. C. Zook, A. K. Didolkar, K. Sundaram, and H. A. Nash. "The Roles of Estrogen and Progestin in Producing Deciduosarcoma and Other Lesions in the Rabbit." *Toxicologic Pathology* 29.4 (2001): 417-421), a common response to estrogenic compounds, was seen to at least a minimal degree in all uterus samples and two spleens from the P36 Active group females. The decidual reaction occurs both within the subendometrial stroma as well as the blood vessels within the uterus. In rabbits with severe affected vessels, there was associated ischemic necrosis of the adjacent uterine tissue due to the disrupted blood supply. This necrosis was occasionally transmural, and in one rabbit, resulted in fibrosis on the abdominal surface of the uterus and adhesion to the parietal surface of the abdominal cavity.

Also in females, three of the animals in the P36 Active group had cysts on the oviducts. Cysts are not uncommon in various female reproductive organs, so it is possible that these cysts may represent developmental anomalies, however the presence of these cysts in three P36 Active group females and no control animals suggests that this alteration may be related to the administration of the test article.

There were no significant differences between the K36 Active and P36 Active treatment groups.

In general, these findings are commonly associated with administration of test composition containing estrogens, and so do not undermine the potential clinical usefulness of the specific formulations described herein.

Example 10: Dose-Escalation Study in 12 Healthy Human Male Subjects

A multiple-dose, open-label, dose-escalation study was designed in which 12 healthy male subjects were scheduled to receive 1 of 2 treatments once daily for 3 days with an 11-day washout period between doses.

The objective of this Phase 1 study was to assess the safety and pharmacokinetic (PK) profile of multiple dose administration of 0.25 g and 1.00 g of a 0.07% transdermal estradiol gel in healthy male volunteers. The transdermal gel used had the following formulation:

| | |
|---|---|
| 0.07% | estradiol |
| 2.0% | ethyl oleate |
| 2.0% | oleic acid |
| 5.0% | propylene glycol |
| 16.91% | purified water |
| 71.94% | ethanol |
| 2.0% | PEMULEN ® TR-1 Carbomer |
| 0.07% | sodium carbonate anhydrous |
| 0.007% | sodium bicarbonate anhydrous |

Twelve (12) healthy subjects were enrolled and participated in two open-label treatment periods. Subjects who successfully completed the screening process checked into the research center on Day 1, approximately 1 to 2 hours prior to the first blood draw of each treatment period. For Treatment Period A, 0.25 g of the 0.07% gel was to be administered once daily for three days. During Treatment Period B, 1.0 g of the 0.07% gel was to be administered once daily for three days. Dosing days were to be separated by a washout period of at least 11 days.

Diagnosis and Main Criteria for Inclusion: Healthy adult male volunteers, 18-45 years of age, with body mass index (BMI) between 18 and 30 kg/m2, inclusive, and minimum weight of 50 kg (110 pounds).

Results:

SYNOPSIS TABLE 1

Parameters of Estradiol

| | Dose | | | | | | | |
|---|---|---|---|---|---|---|---|---|
| | 0.25 g | | | | 1.00 g | | | |
| | N | Mean | SD | CV % | n | Mean | SD | CV % |
| Tmax0-24 (hr) | 12 | 12.83 | 10.14 | 79.04 | 11 | 6.91 | 5.97 | 86.33 |
| Tmax24-48 (hr) | 12 | 32.67 | 9.59 | 29.34 | 11 | 28.18 | 2.89 | 10.24 |
| Tmax48-72 (hr) | 12 | 51.17 | 3.64 | 7.11 | 11 | 54.91 | 6.16 | 11.21 |
| Tmax0-120 (hr) | 12 | 33.58 | 18.68 | 55.63 | 11 | 29.82 | 20.66 | 69.28 |
| Tmax-overall (hr) | 12 | 54.83 | 56.78 | 103.56 | 11 | 29.82 | 20.66 | 69.28 |
| Cmax0-24 (pg/mL) | 12 | 26.4 | 7.35 | 27.83 | 11 | 56.5 | 20.8 | 36.74 |
| Cmax24-48 (pg/mL) | 12 | 29.7 | 11.3 | 38.04 | 11 | 52.1 | 27.3 | 52.43 |
| Cmax48-72 (pg/mL) | 12 | 28.5 | 15.1 | 52.95 | 11 | 49.2 | 22.5 | 45.73 |
| Cmax0-120 (pg/mL) | 12 | 33.1 | 16.5 | 50.02 | 11 | 64.6 | 27.1 | 42.04 |
| Cmax-overall (pg/mL) | 12 | 33.1 | 16.5 | 49.85 | 11 | 64.6 | 27.1 | 42.04 |
| AUC0-24 (hr * pg/mL) | 12 | 476.7 | 115.2 | 24.16 | 11 | 752.2 | 238.9 | 31.76 |
| AUC24-48 (hr * pg/mL) | 12 | 502.7 | 135.9 | 27.04 | 11 | 661.0 | 249.0 | 37.67 |
| AUC48-72 (hr * pg/mL) | 12 | 476.8 | 156.8 | 32.88 | 11 | 658.1 | 252.5 | 38.36 |
| AUC0-120 (hr * pg/mL) | 12 | 2333 | 642.1 | 27.52 | 11 | 2933 | 889.1 | 30.31 |
| AUC0-t (hr * pg/mL) | 12 | 3778 | 1260 | 33.35 | 11 | 4436 | 1204 | 27.14 |
| Tlast (hr) | 12 | 200.27 | 37.50 | 18.73 | 11 | 216.00 | 0.00 | 0.00 |
| Clast (pg/mL) | 12 | 17.3 | 3.87 | 22.37 | 11 | 17.2 | 5.09 | 29.53 |

Conclusion:

Mean baseline concentrations of estradiol ranged from 14.3 pg/mL to 21.7 pg/mL. After administration of 0.25 g of gel, estradiol concentrations increased slightly above baseline (highest mean plasma concentration=25.6 pg/mL). After administration of 1.00 g of gel, estradiol concentrations increased by approximately 2- to 3-fold (highest mean plasma concentration=54.3 pg/mL). In general, concentrations of estradiol returned to baseline levels at approximately 12 hr post-dose for the 0.25 g of gel; for the 1.00 g of gel, concentrations of estradiol returned to baseline levels at approximately 96 hr and 120 hr.

In general, estradiol Tmax after 1.00 g was shorter than that after 0.25 g. Estradiol Tmax was observed between approximately 3 hr (0.25 g, third dosing interval) and 13 hr (0.25 g, first dosing interval) after administration of the gel.

Within each dose group, mean estimates of AUC for each 24-hr dosing interval (AUC0-24) were comparable, indicating no significant accumulation for estradiol. There was a less than proportional increase in exposure to estradiol with an increase in the gel dose.

The increase in peak and overall systemic exposure to estradiol after a 4.00-fold increase in gel dose was 1.95-fold based on Cmax0-120 and 1.26-fold based on AUC0-120.

The ratios (0.25 g: 1.00 g) (90% confidence intervals) for estradiol Cmax0-120 and AUC0-120 were 47.89% (40.17%, 57.10%) and 80.01% (70.45%, 90.88%), respectively.

Example 11: Dose-Escalation Study in 12 Healthy Human Male Subjects

The primary objective of this Phase 1 study was to compare the pharmacokinetic (PK) profiles of two different formulations of transdermal estradiol gel in healthy male volunteers. The secondary objective of this study was to assess the incidence and severity of adverse events.

This was a multiple-dose, open-label, two-treatment study that has been conducted in two parts to evaluate the pharmacokinetics of estradiol after transdermal administration of two different formulations to healthy male volunteers.

12 healthy adult male subjects participated in 2 randomized treatment periods. During each Treatment Period, either 1.25 g of 0.06% ESTROGEL® (estradiol gel) or 1.0 g of a 0.07% estradiol gel according to the invention (formulation in the Table below) were administered once daily to the subject's upper arm for five days. Subjects were randomized to receive either Treatment Code A or B during the first treatment period and the opposite treatment code during the second treatment period. Treatment periods 1 and 2 were separated by a 3 day washout period.

Subjects remained confined in the research center for blood draws for at least 24 hours after the last study gel application in each treatment period, and returned to the research center for blood draws and other study procedures on Days 7 and 8.

| | |
|---|---|
| 0.07% | estradiol |
| 0.3% | ethyl oleate |
| 0.3% | oleic acid |
| 0.75% | propylene glycol |
| 16.91% | purified water |
| 79.59% | ethanol |
| 2.0% | PEMULEN ® TR-1 Carbomer |
| 0.07% | sodium carbonate anhydrous |
| 0.007% | sodium bicarbonate anhydrous |

| Treatment Code | Treatment Intervention |
|---|---|
| A: | Drug: ESTROGEL ® (0.06%)<br>Dose = 1.25 g × 0.6 mg/g = 0.75 mg estradiol<br>Topical, once daily for five days<br>24 hours between dose applications<br>Application site: upper arm<br>Target plasma level: approximately 80 pg/mL |
| B: | Drug: 0.07% estradiol test gel<br>Dose = 1.0 g × 0.7 mg/g = 0.7 mg estradiol<br>Topical, once daily for five days<br>24 hours between dose applications<br>Application site: upper arm<br>Target plasma level: approximately 80 pg/mL |

During each treatment period, blood samples were collected for measurement of estradiol prior to each dose and following each dose at selected times through 72 hours post-dose. Up to 102 blood samples (~510 mL whole blood) were obtained from each subject for pharmacokinetic assessments, excluding screening and post-treatment safety assessments. During Periods 1 and 2, all blood samples were collected from the contralateral arm on which the study gel is being administered, to prevent sample contamination.

Prior to progression to the next treatment period, safety data (adverse events, clinical laboratory tests) will be reviewed before dosing commences.

For all treatment periods, subjects were required to shower/bathe approximately 1 hour prior to each application of the study gel. Showering/bathing privileges were suspended until 1 hour before the next application of the study gel. Each dose was applied topically to the designated application site. After dosing, no food was allowed until two hours post-dose. Water was withheld for one hour post dose and then allowed ad lib for the remainder of the confinement period. Subjects were served meals at approximately the same time relative to dose for each treatment period; the same menu choices were available during all treatment periods. Bathroom/washroom privileges were suspended for one hour after dosing.

Results:

A summary of pharmacokinetic parameters for estradiol after topical application of the test gel at 0.7 mg QD×5 days and ESTROGEL® 0.75 mg QD×5 days to healthy male volunteers is provided in the table below.

|  | Test Gel | ESTROGEL ® |
| --- | --- | --- |
| Estradiol* | (0.7 mg QD × 5 days) | (0.75 mg QD × 5 days) |
| Cmax (pg/mL)† | 65.0 ± 19.4 (10) | 55.6 ± 18.2 (10) |
| Tmax (h)† | 74.0 (10) | 85.5 (10) |
|  | [8.0-98.0] | [2.0-112] |
| AUC(0-t) (h × pg/mL)‡ | 4,131 ± 1,194 (10) | 4,043 ± 654 (10) |

*Arithmetic mean ± standard deviation (N) except Tmax for which the median (N) [Range] is reported.
†Absolute Cmax and Tmax across all doses.
‡AUC from the first through last doses.

Both Examples 10 and 11, where the gels disclosed herein were tested in human clinical trials, demonstrated that the formulations are safe and effective at delivering the drug of interest systematically to patients.

The invention claimed is:

1. A sustained release pharmaceutical composition for topical administration of dihydrotestosterone (DHT) to a skin surface comprising:
   DHT in an amount of 0.2 to 0.5% by weight of the total weight of the pharmaceutical composition;
   a fatty acid ester in an amount of about 2% by weight of the total weight of the pharmaceutical composition;
   water;
   a C2-C6 monoalcohol;
   oleic acid in an amount of about 2% by weight of the total weight of the pharmaceutical composition; and
   a gelling agent in an amount of 0.05% to 5% by weight of the total weight of the pharmaceutical composition,
   wherein the fatty acid ester is ethyl oleate and the weight:weight ratio of the fatty acid ester in the composition to the DHT in the composition is at least 4:1 fatty acid ester:DHT.

2. The composition of claim 1, further comprising a co-solvent present in an amount ranging from 0.01% to 7% by weight of the total weight of the pharmaceutical composition.

3. The composition according to claim 1, wherein the C2-C6 monoalcohol is selected from ethanol, n-propanol, isopropanol, n-butanol, isobutanol, tert-butanol, and mixtures thereof, and is present in an amount ranging from 10% to 90% by weight of the total weight of the pharmaceutical composition.

4. The composition according to claim 1, wherein the alcohol is ethanol.

5. The composition according to claim 1, wherein the weight:weight ratio of the fatty acid ester in the composition to the DHT in the composition is from 4:1 to 20:1 fatty acid ester:DHT.

6. The composition according to claim 1, wherein the composition further comprises propylene glycol in an amount of about 5% by weight of the total weight of the pharmaceutical composition.

7. A method for providing a sustained release of DHT through the skin of a subject, comprising topically administering to the skin of the subject a pharmaceutical composition according to claim 1.

8. The composition according to claim 1, wherein the composition is prepared with a base.

9. The composition according to claim 1, wherein the composition is prepared with a base selected from one or more of sodium hydroxide, triethanolamine, ammonium hydroxide, potassium hydroxide, arginine, aminomethylpropanol, tromethamine, and mixtures thereof.

10. The composition according to claim 1, wherein the composition comprises:
    0.2% DHT, by weight of the total weight of the pharmaceutical composition;
    about 2% ethyl oleate, by weight of the total weight of the pharmaceutical composition;
    about 2% oleic acid, by weight of the total weight of the pharmaceutical composition;
    about 5% propylene glycol, by weight of the total weight of the pharmaceutical composition;
    0.05% to 5% of a gelling agent, by weight of the total weight of the pharmaceutical composition;
    ethanol, and
    water.

11. The composition according to claim 1, wherein the composition comprises:
    0.2% DHT, by weight of the total weight of the pharmaceutical composition;
    about 2% ethyl oleate, by weight of the total weight of the pharmaceutical composition;
    about 2% oleic acid, by weight of the total weight of the pharmaceutical composition;
    about 5% propylene glycol, by weight of the total weight of the pharmaceutical composition;
    0.05% to 5% of a gelling agent, by weight of the total weight of the pharmaceutical composition;
    ethanol,
    sodium hydroxide, and
    water.

12. The composition according to claim 1, wherein the composition comprises:
    0.5% DHT, by weight of the total weight of the pharmaceutical composition;
    about 2% ethyl oleate, by weight of the total weight of the pharmaceutical composition;

about 2% oleic acid, by weight of the total weight of the pharmaceutical composition;
about 5% propylene glycol, by weight of the total weight of the pharmaceutical composition;
0.05% to 5% of a gelling agent, by weight of the total weight of the pharmaceutical composition;
ethanol, and
water.

13. The composition according to claim 1, wherein the composition comprises:
0.5% DHT, by weight of the total weight of the pharmaceutical composition;
about 2% ethyl oleate, by weight of the total weight of the pharmaceutical composition;
about 2% oleic acid, by weight of the total weight of the pharmaceutical composition;
about 5% propylene glycol, by weight of the total weight of the pharmaceutical composition;
0.05% to 5% of a gelling agent, by weight of the total weight of the pharmaceutical composition;
ethanol,
sodium hydroxide, and
water.

* * * * *